(12) United States Patent
Tai et al.

(10) Patent No.: US 11,475,987 B2
(45) Date of Patent: Oct. 18, 2022

(54) WEARABLE INDUCTIVE DAMPING SENSOR

(71) Applicant: California Institute of Technology, Pasadena, CA (US)

(72) Inventors: Yu-Chong Tai, Pasadena, CA (US); Tzu-Chieh Chou, Pasadena, CA (US); Shane S. Shahrestani, Yorba Linda, CA (US)

(73) Assignee: California Institute of Technology, Pasadena, CA (US)

( * ) Notice: Subject to any disclaimer, the term of this patent is extended or adjusted under 35 U.S.C. 154(b) by 408 days.

(21) Appl. No.: 16/568,059

(22) Filed: Sep. 11, 2019

(65) Prior Publication Data

US 2020/0082926 A1    Mar. 12, 2020

Related U.S. Application Data

(60) Provisional application No. 62/730,351, filed on Sep. 12, 2018.

(51) Int. Cl.
| | |
|---|---|
| *G16H 20/30* | (2018.01) |
| *G16H 50/20* | (2018.01) |
| *G01N 27/04* | (2006.01) |
| *G01R 27/26* | (2006.01) |
| *A61B 5/00* | (2006.01) |
| *A61B 5/242* | (2021.01) |

(Continued)

(52) U.S. Cl.
CPC ............ *G16H 20/30* (2018.01); *A61B 5/242* (2021.01); *A61B 5/243* (2021.01); *A61B 5/245* (2021.01); *A61B 5/7278* (2013.01); *G01N 27/041* (2013.01); *G01R 27/2611* (2013.01); *G16H 50/20* (2018.01); *A61B 2562/0223* (2013.01)

(58) Field of Classification Search
CPC combination set(s) only.
See application file for complete search history.

(56) References Cited

U.S. PATENT DOCUMENTS

| | | |
|---|---|---|
| 6,746,785 B1 | 6/2004 | Werner |
| 8,801,646 B2 | 8/2014 | Han et al. |

(Continued)

OTHER PUBLICATIONS

RamRakhyan, et al., "Design and Optimization of Resonance-Based Efficient Wireless Power Delivery Systems for Biomedical Implants", IEEE Transactions on Biomedical Circuits and Systems, vol. 5, No. 1, Feb. 2011. (Year: 2011).*

(Continued)

*Primary Examiner* — Amber A Misiaszek
(74) *Attorney, Agent, or Firm* — Kilpatrick Townsend & Stockton LLP

(57) ABSTRACT

Techniques are described for a non-invasive detection of a health condition of an organ. In an example, the electrical conductivity of the organ reflects the organ's health of. An inductive damping sensor can be used to detect the organ's electrical conductivity and, thus, its health. The inductive damping sensor can be placed in proximity of the organ such as the organ is within the magnetic field generated based on a coil of the inductive damping sensor. The conductivity of the organ impacts the inductance and the resistance of the coil. Hence, the inductance and/or resistance of the coil can be measured, where the measurements can be associated with the health of the organ.

20 Claims, 17 Drawing Sheets

(51) Int. Cl.
  *A61B 5/243* (2021.01)
  *A61B 5/245* (2021.01)

(56) References Cited

U.S. PATENT DOCUMENTS

| | | | | |
|---|---|---|---|---|
| 2009/0112115 | A1* | 4/2009 | Huang | A61B 5/083 |
| | | | | 600/532 |
| 2011/0193575 | A1 | 8/2011 | Rubinsky et al. | |
| 2011/0245707 | A1 | 10/2011 | Castle et al. | |
| 2013/0123585 | A1 | 5/2013 | Kang | |
| 2014/0358016 | A1 | 12/2014 | Shapira et al. | |
| 2015/0339421 | A1* | 11/2015 | Srinivasan | G06F 30/39 |
| | | | | 716/139 |
| 2016/0343497 | A1* | 11/2016 | Clark | H01C 10/30 |
| 2017/0319099 | A1* | 11/2017 | Levinson | A61B 5/7246 |
| 2018/0064364 | A1 | 3/2018 | Oziel et al. | |
| 2018/0230538 | A1 | 8/2018 | Stamova-Kiossepacheva et al. | |
| 2018/0239430 | A1 | 8/2018 | Tadi et al. | |
| 2020/0082926 | A1 | 3/2020 | Tai et al. | |

OTHER PUBLICATIONS

PCT/US2019/050654, "International Preliminary Report on Patentability", dated Mar. 25, 2021, 9 pages.
PCT/US2021/018560, "International Search Report and Written Opinion", dated May 6, 2021, 17 pages.
PCT/US2019/050654, "International Search Report and Written Opinion", dated Nov. 8, 2019, 10 pages.
"How to Use Vscan to Measure Urinary Bladder", GE Healthcare, Available online at: https://www.youtube.com/watch?v=35Lda53ZuK0, Aug. 7, 2015, 3 pages.
"LDC1612, LDC1614 Multi-Channel 28-Bit Inductance to Digital Converter (LDC) for Inductive Sensing", Texas Instruments, Available online at: http://www.ti.com/lit/ds/symlink/ldc1612.pdf, Mar. 2018, 67 pages.
Beynon, "A Glimmer of Hope for a Devastating Complication", Blood, vol. 129, No. 22, Jun. 1, 2017, pp. 2952-2953.
Gabriel et al., "Electrical Conductivity of Tissue at Frequencies Below 1 Mhz", Physics in Medicine and Biology, vol. 54, 2009, pp. 4863-4878.
Garcia-Martin et al., "Non-Destructive Techniques Based on Eddy Current Testing", Sensors, vol. 11, No. 3, 2011, pp. 2525-2565.
Giovangrandi et al., "Ballistocardiography—A Method Worth Revisiting", Conference Proceedings, IEEE Engineering in Medicine and Biology Society, Aug. 2011, pp. 4279-4282.
Grieten, "FibriCheck Beat-to-Beat Accuracy Compared with Wearable ECG in Broad Dynamic Range", Available online at: https://www.fibricheck.com/fibricheck-beat-to-beat-accuracy-compared-with-wearable-ecg-in-broad-dynamic-range/12, Jun. 20, 2019, 17 pages.
Lin, "Radiation Risk from Medical Imaging", Mayo Clin. Proc., vol. 85, No. 12, Dec. 2010, pp. 1142-1146.
Nabavi et al., "Design Strategies for Eddy-Current Displacement Sensor Systems: Review and Recommendations", IEEE Sensors Journal, vol. 12, No. 12, Dec. 2012, pp. 3346-3355.
Oberhauser, "Optimizing L Measurement Resolution for the LDC161X and LDC1101", Texas Instruments, Available online at: http://www.ti.com/lit/an/snoa944/snoa944.pdf, Feb. 2016, 9 pages.
Robertson et al., "Clinical Evaluation of a Portable Near-Infrared Device for Detection of Traumatic Intracranial Hematomas", Journal of Neurotrauma, vol. 27, No. 9, Sep. 2010, pp. 1597-1604.
PCT/US2021/018560, "International Preliminary Report on Patentability", dated Dec. 14, 2021, 16 pages.

* cited by examiner

WEARABLE INDUCTIVE DAMPING SENSOR

CROSS-REFERENCES TO RELATED APPLICATIONS

This application claims the benefit of U.S. Provisional Application No. 62/730,351, filed Sep. 12, 2018, the contents of which are hereby incorporated in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

By nature, living beings are subject to diseases. Many of the diseases can be fatal or cause a great amount of pain. Tremendous effort has been invested in developing technologies to diagnose and treat the diseases. However, many of such technologies can be complex to use or even invasive.

For example, a human may suffer from a hemorrhagic stroke, in which a vessel ruptures in the brain and leads to excessive bleeding. The bleeding can compress areas of the brain and prevent adequate perfusion, leading to cell death. To diagnose whether the hemorrhagic stroke actually occurred or not, the human can be placed inside a magnetic resonance imaging (MRI) machine that generates images of the brain. A physician can identify an area where the bleeding may be occurring from the images.

In another example, edema is the abnormal accumulation of fluid in certain tissues within a body of the human. The accumulation of fluid may be under the skin, such as in the legs (peripheral edema, or ankle edema), or it may accumulate in the lungs (pulmonary edema). To diagnose edema, X-rays, blood tests, urine tests, and/or an echocardiogram can be performed.

In both examples, the complexity of the diagnosis techniques typically necessitates physical examination by a trained physician. In addition, the complexity can hinder the capability of continuous monitoring outside of the physical examination and, thus, the capability of performing preventive treatment.

As such, there is a need in the art for diagnosis techniques that are less complex.

BRIEF SUMMARY

Techniques are described for a non-invasive detection of a health condition of an organ. In an example, a sensor system is used for the non-invasive detection. The sensor system includes an inductive damping sensor including a coil that has an inductance and a resistance. The inductive damping sensor is configured to generate a magnetic field based on the coil, measure at least one of the inductance or the resistance based on a counteracting magnetic field from an organ located within the magnetic field, and output data that indicates the at least one of the inductance or the resistance. The sensor system also includes a computer system communicatively coupled with the inductive damping sensor and including a processor and a memory. The memory stores computer-readable instructions that, upon execution by the processor, cause the computer system to receive the data and determine a health condition of the organ based on the least one of the inductance or the resistance of the coil as indicated by the data.

In an example, the inductive damping sensor further includes a capacitor in parallel with the coil, an inductance-to-digital converter in parallel with the coil, and a microcontroller communicatively coupled with the inductance-to-digital converter. The inductance-to-digital converter is configured to measure an eddy current in the coil and output digitized data that indicates at least one of the inductance or the resistance based on the eddy current. The microcontroller is configured to receive the digitized data and store the digitized data as the data that indicates the at least one of the inductance or the resistance.

In an example, the coil includes loops of a conductive wire around a cylindrical core. A total number of the loops is in the range of two to fifty. A diameter of the cylindrical core is in the range of one centimeter to twenty centimeters.

In an example, the coil includes a number of loops and has a diameter. The sensor system further includes a second inductive damping sensor. The second inductive damping sensor includes a second coil. The second coil includes a different number of loops and has a different diameter. Determining the health condition includes determining a location of the health condition within the organ based on the coil and the second coil.

In an example, determining the health condition includes determining a change in the at least one of the inductance or the resistance of the coil. The change includes at least one of a decrease of the inductance or an increase of the resistance. Determining the health condition also includes determining a change in a conductivity of the organ based on at least one of the decrease of the inductance or the increase of the resistance. The execution of the computer-readable instructions further configure the computer system to associate the change in the conductivity of the organ with an increase of a conductive fluid in the organ. The execution of the computer-readable instructions further configure the computer system to associate the change in the conductivity of the organ with a volume of a conductive fluid in the organ.

In an example, determining the health condition includes determining at least one of a location or a volume of a conductive fluid in the organ. The conductive fluid causes the health condition.

In an example, determining the health condition includes determining a change in the at least one of the inductance or the resistance of the coil. The change includes at least one of an increase of the inductance or a decrease of the resistance. Determining the health condition also includes determining a change in a conductivity of the organ based on at least one of the increase of the inductance or the decrease of the resistance.

In an example, the organ includes a heart. The health condition includes at least one of a blood flow of the heart, a pulse rate of the heart, or an ejection fraction of the heart.

In an example, the organ includes a brain. The health condition includes a hemorrhagic stroke of the brain or an ischemic stroke of the brain.

In an example, the organ includes a brain. The health condition includes an intracranial hemorrhage within the brain. Determining the health condition includes determining a change in the at least one of the inductance or the resistance of the coil, and generating a mapping of the brain based on the change in at least one of the inductance or the resistance of the coil. The mapping indicates a location of the intracranial hemorrhage.

In an example, the health condition indicates skin edema based on the data indicating a decrease of the inductance or an increase of the resistance.

In an example, the health condition indicates a hemorrhage within the organ based on the data indicating a decrease of the inductance or an increase of the resistance.

In an example, the organ includes a liver. Determining the health condition includes determining a change to a conductivity of the liver based on the data indicating a decrease of the inductance or an increase of the resistance.

In an example, the health condition indicates a respiratory rate based on the data indicating a decrease of the inductance or an increase of the resistance.

In an example, the health condition indicates location of a vein or an artery based on the data indicating a decrease of the inductance or an increase of the resistance.

In an example, a sensor can be used for the non-invasive detection. The sensor includes a coil configured to generate a magnetic field based on electrical coupling with a power source. The sensor also includes an inductance-to-digital converter electrically coupled with the coil and configured to measure a least one of an inductance of the coil or a resistance of the coil based on a counteracting magnetic field from an organ located within the magnetic field. The sensor also includes a microcontroller configured to store data that indicates at least one of the measured inductance or the measured resistance. A health condition of the organ is generated based on the data.

In an example, the coil includes loops of a conductive wire around a cylindrical core. A total number of the loops is in the range of two to fifty. A diameter of the cylindrical core is in the range of one centimeter to twenty centimeters. The cylindrical core is a ferrite core.

In an example, the non-invasive detection relies on a method of using an inductive damping sensor. The method includes placing the inductive damping sensor in proximity of an organ. The inductive damping sensor includes a coil that has an inductance and a resistance. The inductive damping sensor is configured to: generate a magnetic field based on the coil, measure at least one of the inductance or the resistance based on a counteracting magnetic field from the organ located within the magnetic field, and output data that indicates the at least one of the inductance or the resistance. The method also includes turning on power to the inductive damping sensor. The method also includes determining a health condition of the organ based on a presentation of the data on a user interface.

In an example, the health condition includes at least one of: a blood flow of a heart, a pulse rate of the heart, an ejection fraction of the heart, a hemorrhagic stroke of a brain, an ischemic stroke of the brain, an intracranial hemorrhage within the brain, a skin edema, a hemorrhage, a respiratory rate, a location of a vein, or a location of an artery based on the at least one of the inductance or the resistance of the coil.

A further understanding of the nature and the advantages of the embodiments disclosed and suggested herein may be realized by reference to the remaining portions of the specification and the attached drawings.

DETAILED DESCRIPTION

Figure 1:
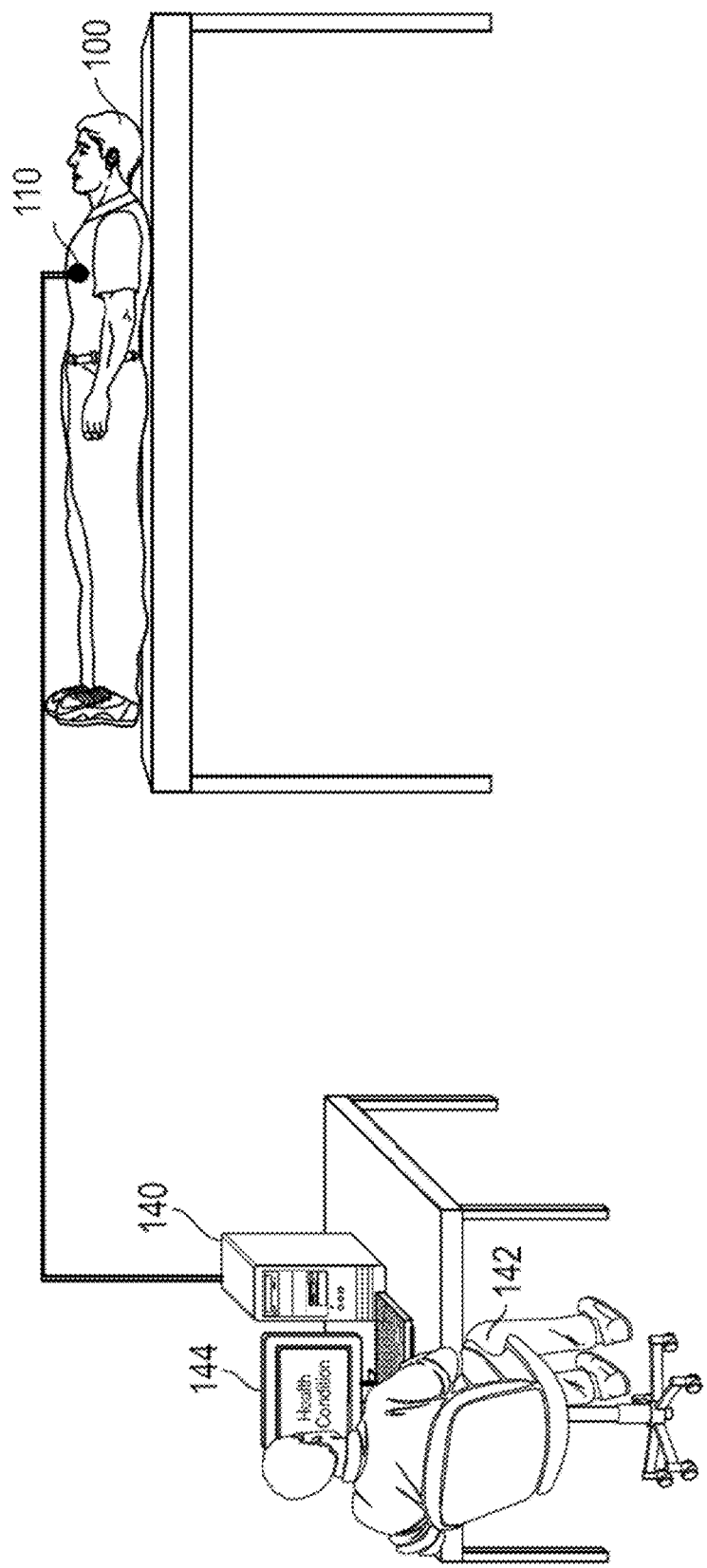
FIG. 1 illustrates an example of a sensor system for health diagnosis in accordance with an embodiment.

Generally, diagnosis techniques are described herein. Particularly described are exemplary diagnosis techniques that rely on a sensor system to diagnose a health condition of a subject, such as a human. The sensor system resolves many of the complexity issues of existing diagnosis system and, if needed, may be partially or fully worn or attached to the subject to allow continuous monitoring of the health condition.

In embodiments, an organ of a subject may be associated with a known conductivity. A change to the conductivity can indicate a health condition of the organ. For example, the organ has a relatively low electrical conductivity, whereas fluid, such as blood or urine, can have a relatively high electrical conductivity. The health of the organ can be diagnosed by measuring its electrical conductivity. In particular, the measured conductivity is expected to be low for a healthy organ. However, if the measured conductivity is high, the organ may not be healthy and the deterioration of its health can be due to the flow or accumulation of the highly conductive fluid within the organ.

Measuring the conductivity of the organ and, thus, diagnosing its health can be performed indirectly by using the sensor system (e.g., by placing, such as wearing, the sensor system in proximity of the organ without having to perform an invasive procedure). The sensor includes an inductive damping sensor. In turn, the inductive damping sensor includes a coil and can generate a magnetic field by flowing an electric current through the coil. When the organ is placed within the magnetic field, a counteracting magnetic field causes a change to the inductance of the coil, or equivalently, an opposite change in the resonance frequency of the coil. The counteracting magnetic field also imposes an electromotive force that impedes the current flow in the coil and, thus, changes the resistance of the coil. The counteracting magnetic field depends on the conductivity of the organ or of the fluid within the organ and the volume of such fluid. The measured inductance and/or resistance of the coil can be correlated with the conductivity of the organ. In other words, the health of the organ can be detected from the measured inductance and/or resistance of the coil.

Many different types of organs and health conditions of such organs can be detected based on the measured inductance and/or resistance of the coil. In one example, the measured inductance and/or resistance can be compared to a baseline. The difference from the baseline indicates whether the organ is healthy or not. In another example, the measured inductance and/or resistance change over time and the change can be monitored to determine a change rate. The change rate indicates whether the organ is healthy or not. In a further example, the measured inductance and/or resistance can be correlated with a volume of fluid within the organ. The volume of the fluid indicates whether the organ is healthy or not. Accordingly, different health conditions can be detected and include a blood flow of a heart, a pulse rate of the heart, an ejection fraction of the heart, a hemorrhagic stroke of a brain, an ischemic stroke of the brain, an intracranial hemorrhage within the brain, a skin edema, a hemorrhage, a respiratory rate, a location of a vein, or a location of an artery based on the at least one of the inductance or the resistance of the coil. In addition, multiple inductive damping sensors can be used to determine location and/or depth of the health condition within the organ.

FIG. 1 illustrates an example of a sensor system for health diagnosis in accordance with an embodiment. As illustrated, the sensor system includes an inductance damping sensor 110 wearable by a subject 100 and a computer system 140 remote from and communicatively coupled with the inductance damping sensor 110. An operator 142, such as a physician, operates the computer system 140 to diagnose the health condition.

The inductance damping sensor 110 can be worn on or placed in proximity of a body or a head of the subject 100 and is not implanted in the subject, thereby avoiding an invasive procedure. In operation, the inductance damping sensor 110 can remain stationary relative to the subject 100 or can be moved around (e.g., to perform a scan) relative to the body and/or head. Measurements about electrical properties, such as inductance and/or resistance of one or more coils of the inductance damping sensor 110, can be collected as measurement data. The measurement data can be stored locally on the inductance damping sensor 110 and, subsequently, uploaded to the computer system 140 and/or can be transmitted in real-time or near real-time to the computer system 140 over a data and, optionally, power interface. The interface between the inductance damping sensor 110 and the computer system 140 can be wireless or wired interface.

The computer system 140 stores computer-readable instructions for a health diagnosis application. Upon execution of the computer-readable instructions on the computer system 140, the health diagnosis application analyzes the measurement data received from the inductance damping sensor 110 over the interface, where the analysis enables a detection of the health condition. The health diagnosis application presents the health condition and/or the measurement data on a user interface 144, such as a display, of the computer system 140.

The different components of the sensor system are illustrated as being separate. Nonetheless, the embodiments of the present disclosure are not limited as such. Instead, some or all of the illustrated components can be integrated as further illustrated in the FIGS. 2-3.

In an example, the inductance damping sensor 110 includes a number of components, such as a number of coils looped around a number of cores and a number of processing circuitries. Example components of the inductance damping sensor 110 are further illustrated in FIGS. 4 and 7. The specific configuration (e.g., number and diameter of loops) depends on a target organ of the subject 100 for which health diagnosis is desired. The target organ can be any of a heart, a brain, a skin, lungs, a vein, or an artery.

Given the specific configuration, the inductance damping sensor 110 is placed in proximity of the target organ (e.g., over the left chest for the heart, over the middle of the chest for lungs, over an ankle for skin edema, over the head for the brain, over an arm for vein or artery, etc.). A magnetic field is generated based on a coil of the inductance damping sensor 110. When the target organ is within the magnetic field given the placement of the inductance damping sensor 110 in proximity of the organ, a counteracting magnetic field is generated based on the conductivity of the target organ. As used herein, conductivity refers to electrical conductivity. The conductivity of the target organ can be a function of the conductivity of the structure of the target organ (e.g., tissues, muscles, etc.) and of the conductivity and amount or volume of fluid within the organ. The counteracting magnetic field results in a change to the inductance and/or resistance of the coil. A processing circuitry of the inductance damping sensor 110 measures the inductance and/or resistance (or the change to the inductance and/or resistance from a pre-designed inductance and/or resistance) based on the eddy current flowing through the coil and collects the measurements as the measurement data.

In an example, the computer system 140 represents a head end computer that analyzes the measurement data (e.g., by executing the health diagnosis application). Generally, the computer system 140 includes a memory, a processor, and a user interface 144 (e.g., one or more of a display, keyboard, mouse, etc.). The measurement data is received by the computer system 140 and stored in the memory. Any suitable memory can be used such as RAM and/or ROM memories. The memory hosts the computer-readable instructions for the health diagnosis application. Such instructions are executed by the processor. Any suitable processor can be used such as a general central processing unit (CPU). The user interface 140 is available to the operator 142 to interface with the health diagnosis application.

The health diagnosis application provides various diagnosis-related functionalities. For example, the health diagnosis application facilitates medical diagnosis based on the measurement data indicative of the electrical properties (e.g., inductance and/or resistance) of the coil(s) of the inductance damping sensor 110. In particular, given the target organ, the health diagnosis application stores information that associates various levels of the electrical properties of the coil(s) with various levels of the conductivity of the target organ. Each level association indicates a health condition of the target organ, such as whether the target organ is healthy or not, an amount or volume of the conductive fluid within the organ, and/or a location of the conductive fluid within the organ. Based on the measurement data and the stored information about the level associations, the health diagnosis application detects the health condition of the target organ and presents the health condition and/or the measurement data on the user interface 140. Examples of the analysis performed on the measurement data based on the target organ are further described in connection with FIGS. 8-15.

Hence, by wearing or placing the inductance damping sensor 110 in proximity of the subject 100 and by operating the computer system 140, the operator 142 can diagnose a health condition of the subject 100 based on the electrical properties of coil(s) of the inductance damping sensor 110. Such a diagnosis technique is not invasive and is simple to perform.

Figure 2:
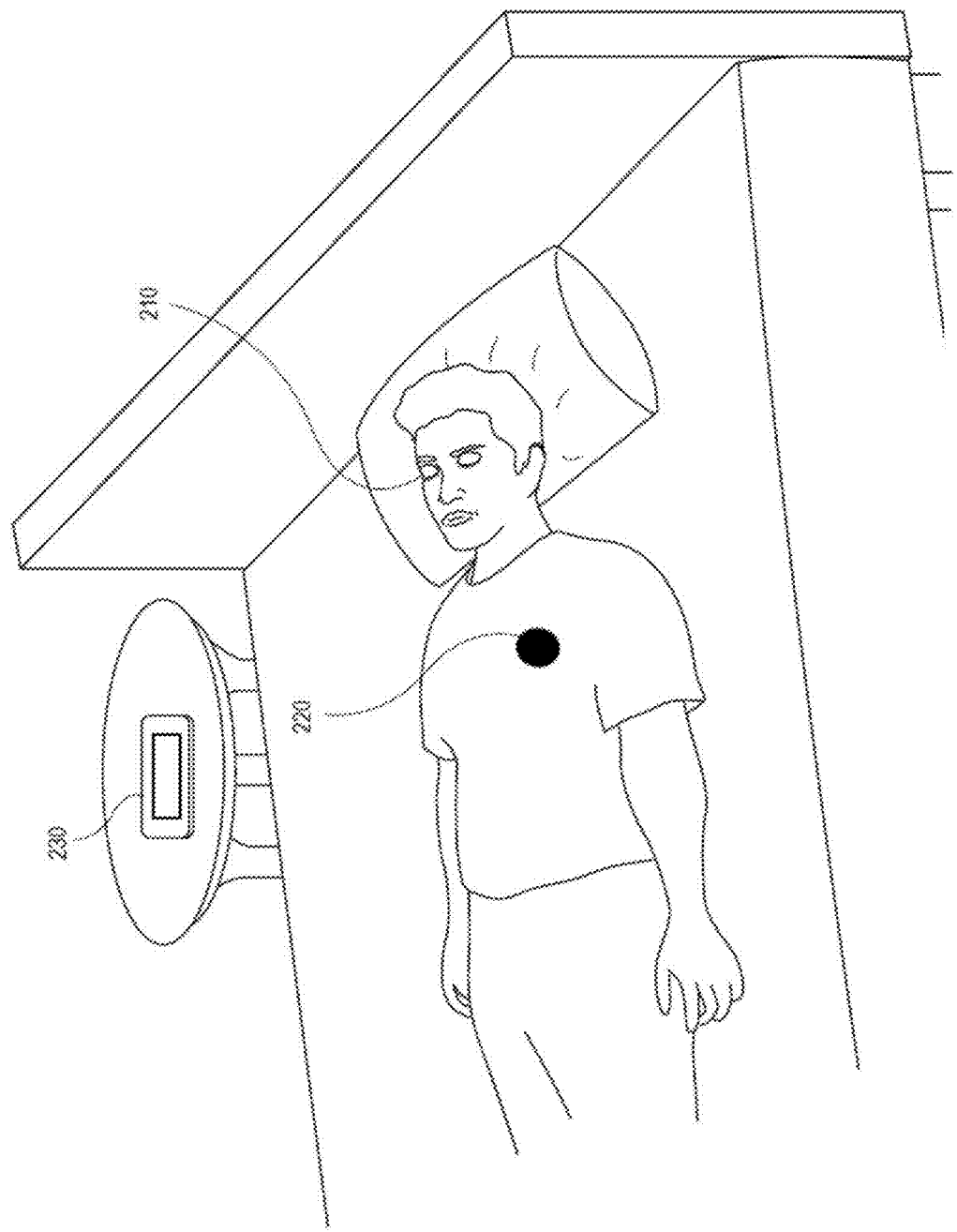
FIG. 2 illustrates another example of a sensor system for health diagnosis in accordance with an embodiment.

FIG. 2 illustrates another example of a sensor system for health diagnosis in accordance with an embodiment. Here, the sensor system may be fully operated by a subject 210 and need not involve a trained operator. Nonetheless and similarly to the illustration of FIG. 1, the sensor system of FIG. 2 is a distributed system that includes an inductance damping sensor 220 and a computer system 230 that are separate from each other and that are communicatively coupled with each other.

As illustrated, the inductance damping sensor 220 can be worn on the body or the head of the subject 210 or can be placed in proximity to the body or the head. In particular and without an invasive procedure, the inductance damping sensor 220 is located next to a target organ for which a health diagnosis is desired. The inductance damping sensor 220 collects measurement data and transmits such data over a wireless interface, such as BLUETOOTH or WI-FI, to the computer system 230.

The computer system 230 can be a smartphone, a tablet, a laptop, a personal computer, or any other user device that can include a general purpose processor. The computer system 230 hosts a health diagnosis application that analyzes the measurement data and presents the health condition and/or the measurement data on a user interface of the computer system 230.

Figure 3:
FIG. 3 illustrates yet an example of a sensor system for health diagnosis in accordance with an embodiment.

FIG. 3 illustrates yet an example of a sensor system for health diagnosis in accordance with an embodiment. Similarly to the illustration of FIG. 2, the sensor system of FIG. 3 may be fully operated by a subject 310 and need not involve a trained operator. However, the sensor system of FIG. 3 is not a distributed system. Instead, the sensor system includes an inductance damping sensor and a computer system that are separate components of a same wearable device 320.

As illustrated, the wearable device 320 can be worn on the body or the head of the subject 310 or can be placed in proximity to the body or the head. In particular and without an invasive procedure, the wearable device 320 is located next to a target organ for which a health diagnosis is desired. The inductance damping sensor of the wearable device 320 collects measurement data and transmits such data over serial bus to the computer system of the wearable device 320. The computer system hosts a health diagnosis application that analyzes the measurement data and presents the health condition and/or the measurement data on a user interface of the computer system, such as a graphical user interface. The wearable device 320 can also alert the subject 310 when the health condition indicates that the target organ is unhealthy. For the alert, the user interface can alternatively or additionally include an audible interface (e.g., one that plays a sound or a chime to alert the subject 310), or a haptic interface (e.g., one that vibrates to alert the subject 310).

Figure 4:
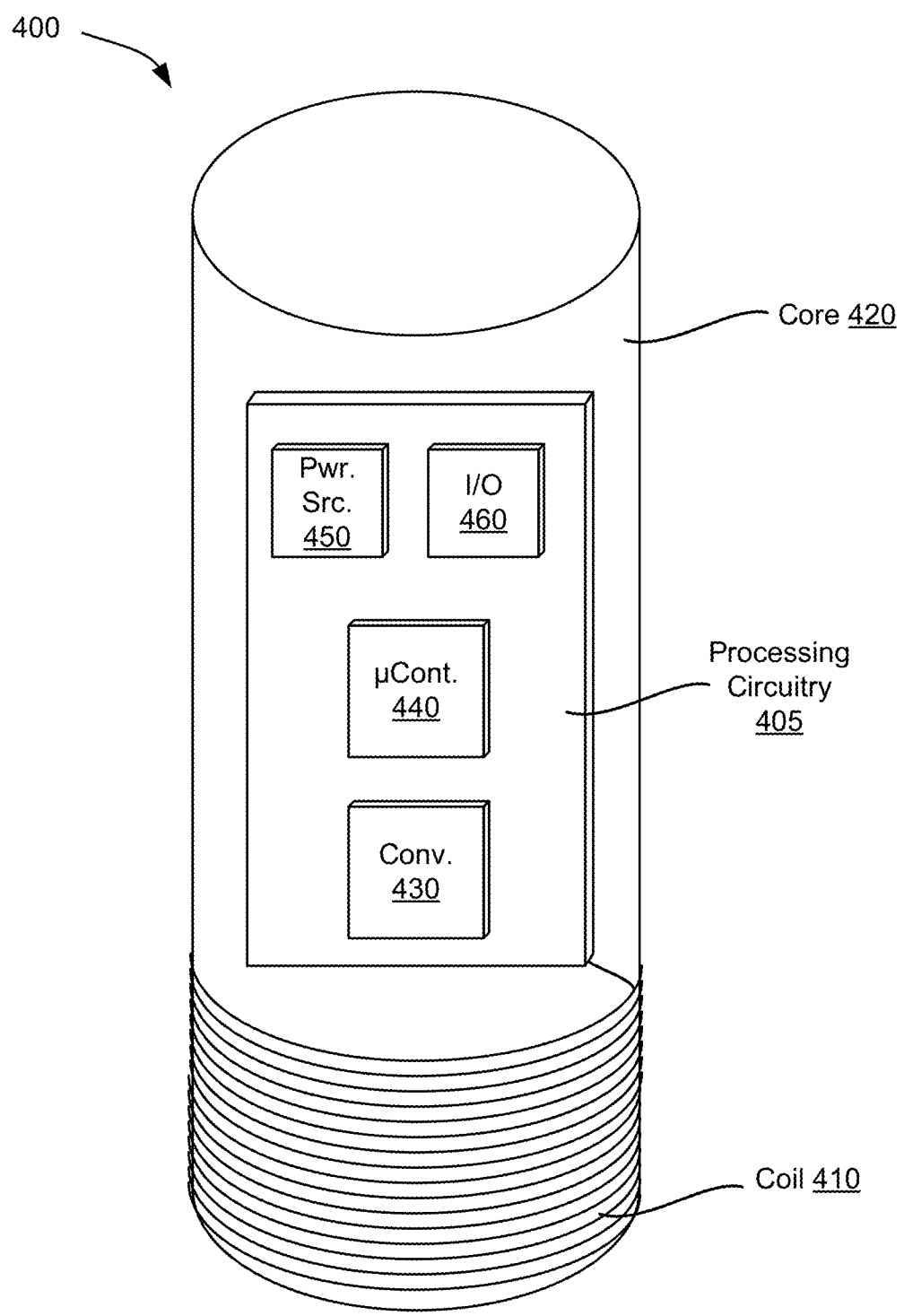
FIG. 4 illustrates examples of components of an inductive damping sensor of a sensor system in accordance with an embodiment.

FIG. 4 illustrates examples of components of an inductive damping sensor 400 of a sensor system in accordance with an embodiment. As illustrated, the components include a processing circuitry 405, a coil 410, and a core 420. Generally, the coil 410 is looped around the core 420 and, upon a current flow, can generate a magnetic field. The processing circuitry 405 may, but need not be attached to or installed within the core 420 and can supply electrical power for the current flow, perform measurements of electrical properties of the coil 410 based on an eddy current through the coil 410, and collect the measurements as measurement data in a digitized format. The electrical properties include at least one of the inductance (or equivalently the resonance frequency) or the resistance of the coil 410.

In an example, the coil 410 includes a conductive wire, such as a litz wire or a copper wire, that loops around at least a portion of the core 420. The total number of loops, among other factors, can vary to achieve a target resonance frequency. The loops can be substantially circular when the core 420 is cylindrical. In this case, the inner diameter of the loops corresponds substantially to the outer diameter of the cylindrical core 420. The size of the diameter (e.g., inner diameter or outer diameter), among other factors such as the total number of loops, can impact the size of the magnetic field (e.g., the depth). Generally, the larger the size is and/or the larger the total number is, the deeper the magnetic field is. In an illustration, the total number of the loops is in the range of two to fifty, the diameter is in the range of one centimeter to twenty centimeters, and the resonance frequency is in the range of 0.5 MHz and 5 MHz.

To avoid or reduce magnetic interference, the core 420 can be made out of a ferrite material. Alternatively, the core 420 can be made of other solid materials, such as plastic or glass. In both cases, ferrite shielding can be applied to the coil 410 to also avoid or reduce magnetic interference. The coil 410 can be secured in different ways to the core 420, such as with glue, mechanical friction (e.g., based on mechanical tightening), and/or in grooves of the core 420.

In an example, the processing circuitry 405 includes a number of components and is electrically coupled with the coil 410 via a wire. These components include an inductance-to-digital converter 430, a microcontroller 440, a power source 450, and an input/output (I/O) interface 460. Such components can be installed on a printed circuit board.

The inductance-to-digital converter 430 measures the electrical properties, including the inductance and resistance, of the coil 410 based on the eddy current flowing through the coil 410. The inductance-to-digital converter 430 converts the measurements into measurement data having a digitized format (e.g., digitized data) and sends the measurement data to the microcontroller 440. An example of the inductance-to-digital converter 430 is an LDC1101 inductance-to-digital converter available from TEXAS INSTRUMENTS headquartered in Dallas, U.S.A.

The microcontroller 440 includes a processor and a memory. The processor stores the measurement data in the memory (e.g., as a log) and can transmit in real-time or near-real time or upload on demand the measurement data to a computer system via the I/O interface 460. The I/O interface 460 can include a universal serial bus (USB), BLUETOOTH, WI-FI or any other type of wired or wireless data interface.

In an example, the power source 450 can include a rechargeable or disposable battery that provides a direct current (DC). In this case, the processing circuitry 405 can also include a DC-to-alternating current (AC) converter to convert the DC current into an AC current, such that a desired AC current is supplied to the coil 410. In another example, the power source 450 may be a power interconnection to an external power source. For instance, the power interconnection can be a USB connector (plug or receptacle) that can be connected to a USB connector of the computer system to receive power (e.g., DC power supplied at 5 VDC) from the computer system. In another illustration, the power interconnection can receive AC power from an external AC power source.

Figure 5:
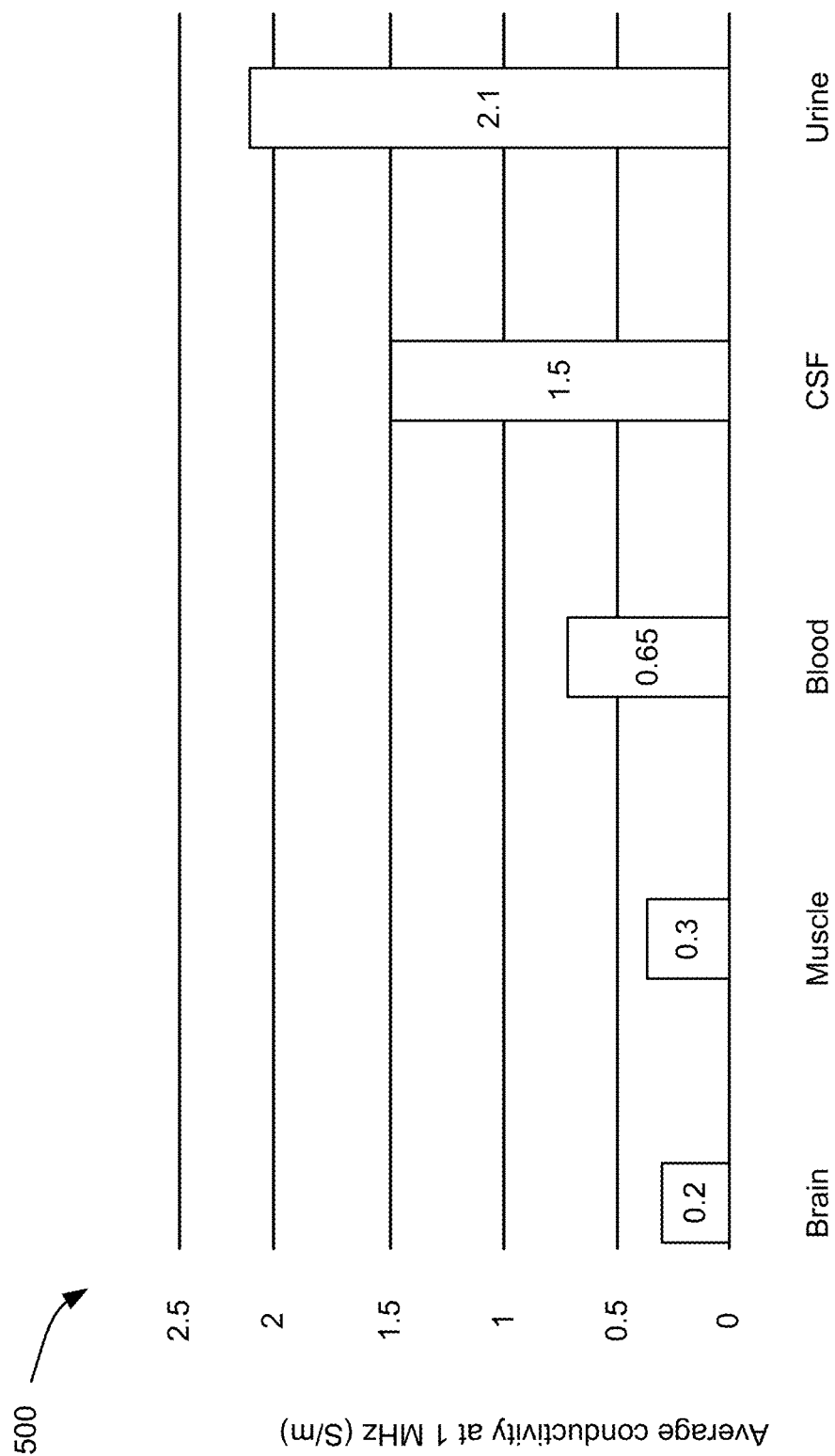
FIG. 5 illustrates examples of conductivity of organs in accordance with an embodiment.

FIG. 5 illustrates examples of conductivity 500 of organs in accordance with an embodiment. Generally, a coil, such as the coil 410 of FIG. 4, carrying an alternating current generates a time-varying magnetic field that induces an electromotive force according to Faraday's law:

$$\nabla \times \vec{E} = -\frac{\partial \vec{B}}{\partial t}.$$

the electromotive force causes a looping current (e.g., an eddy current) to flow in a conductive material according to ohm's law: $\vec{J} = \sigma \vec{E}$, where $\sigma$ is the conductivity of the material. The eddy current flows in the direction such that it changes (e.g., increases) the coil resistance and changes (e.g., decreases) the coil inductance, both of which can be detected by a processing circuitry, such as the processing circuitry 405 of FIG. 4.

Hence, the conductivity (e.g., "$\sigma$") of a target organ may be known a priori for a resonance frequency of the coil. By placing the coil such that the target organ is within the magnetic field, a particular inductance and/or resistance of the coil should be expected. By measuring the inductance and/or resistance of the coil, if the measurements are as expected, the target organ is likely healthy. However, if the measurements diverge from the expected inductance and/or resistance, the target organ is likely unhealthy because of changes to the target organ altering its conductivity. The changes can include a degradation or growth of the structure (e.g., tissues, muscles, etc.) of the target organ or an increase, decrease, or flow of fluid (e.g., blood, urine, etc.) within or around the organ.

By knowing the conductivity of the target organ, it becomes possible to associate the measured inductance and/or resistance with the health condition. FIG. 5 illustrates the conductivity 500 at 1 MHz of the brain and muscles in addition to fluids that can be present in such organs or other organs. The fluids include blood, cerebrospinal fluid (CSF), and urine. As illustrated, the brain is the least conductive, whereas urine is the most conductive.

To illustrate how such conductivities can be used, consider an example of scanning a brain with a sensor system of the present disclosure. Blood hemorrhage may exist in the brain. If existing, the location of the blood hemorrhage contains an amount of blood having more than three times the typical conductivity of the brain. Hence, if the measurements of the inductance and/or resistance indicates a much higher conductivity than the typical brain conductivity, it can be assumed that blood hemorrhage is present.

In another illustration, a volume change of the body fluid inside an organ (e.g. blood in the heart, urine in the bladder, CSF in the brain etc.) can be estimated by knowing the conductivity difference between the target body fluid and surrounding tissue at the sensor resonance frequency.

Depending on the depth of the target organ, the coil needs to be properly sized such that the region of interest in the target organ (e.g. left ventricle of the heart) is covered by the magnetic field while others are not, to maximize the specificity.

Figure 6:
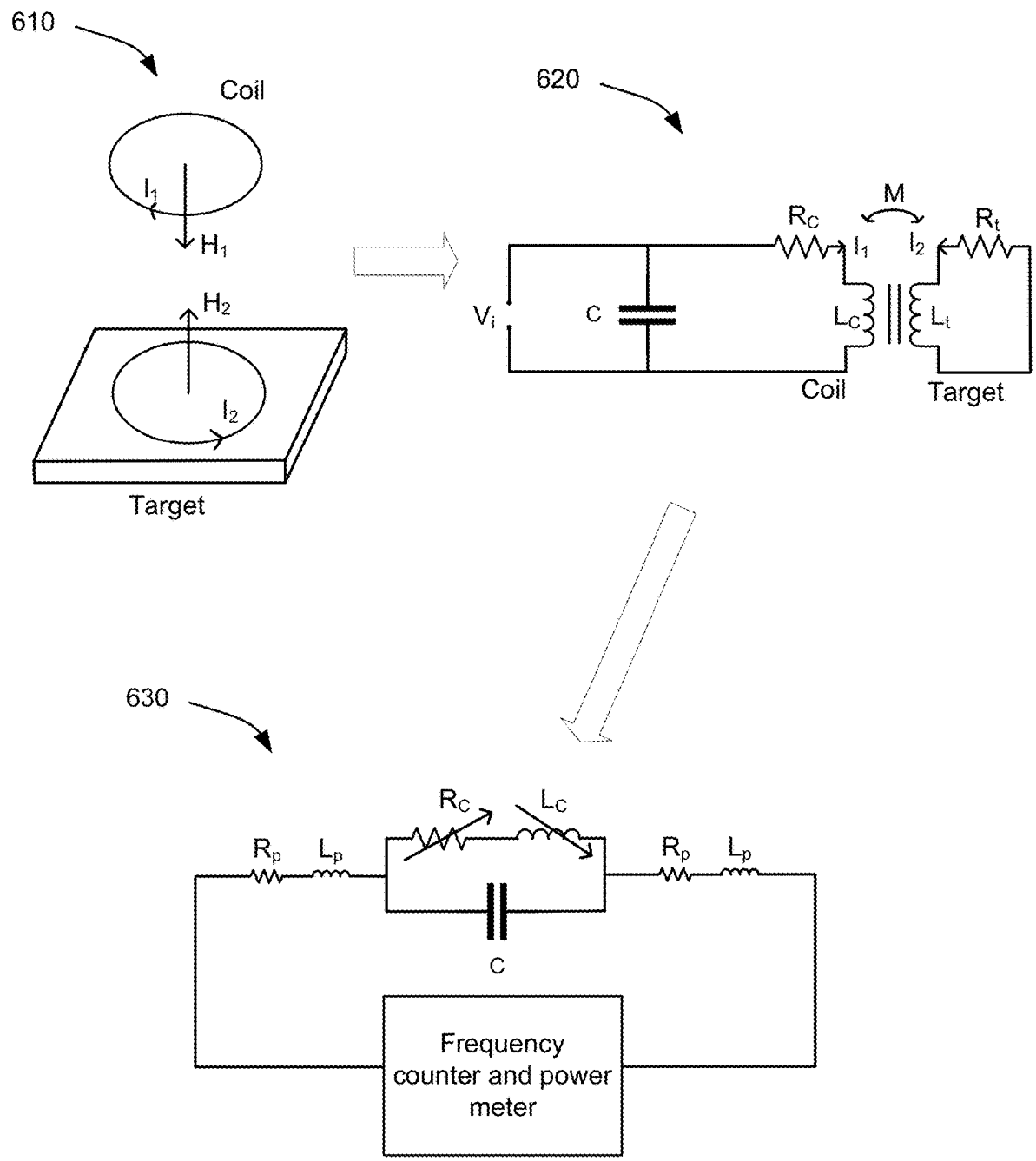
FIG. 6 illustrates an example of modeling an inductive damping sensor in accordance with an embodiment.

FIG. 6 illustrates an example of modeling an inductive damping sensor in accordance with an embodiment. The modeling 610 is based on the magnetic field and counteracting magnetic field between a coil and a conductive target (e.g., an organ) and include a schematic drawing 620 and the equivalent circuit model 630 of the inductive damping sensor. Unlike the traditional eddy current sensor for crack inspection, which consists of a bridge circuit that measures the sensor coil impedance, the inductive damping sensor includes the sensor coil paired with a capacitor to form an electrical resonant circuit. One major advantage of the resonant circuit is the low power consumption for wearable sensors.

As illustrated in the modeling 610, when a conductive target (e.g., blood or urine) is placed in front of the coil, the eddy currents are generated in the target and produce a counteracting magnetic field. This counteracting magnetic field causes a decrease in the coil inductance, or equivalently, a rise in the coil resonant frequency that can be measured by a precise frequency counter. The same counteracting magnetic field also imposes an electromotive force that impedes the current flow in the coil, and thus increasing the coil's AC resistance. This change in coil resistance can be determined by measuring the power dissipation in the coil with a precise power meter. An inductance-to-digital converter can measure the change in coil inductance and coil resistance simultaneously. In other words, the inductance-to-digital converter can include the frequency counter and the power meter.

Accordingly, the schematic drawing 620 of the inductance damping sensor includes a capacitor "C" in parallel with a resistor "$R_C$" and an inductor "$L_C$" that are in series. An AC voltage source can be connected in parallel to the capacitor. The conductive target can be modeled as a closed loop that includes a resistor "$R_t$" and an inductor "$L_t$." Eddy currents "$I_1$" and "$I_2$" flow in the coil and target, respectively, based on the magnetic field and counteracting magnetic field represented as a field "M."

To measure the inductance and the resistance of the coil, the frequency counter and power meter can be connected in parallel across the resistor "$R_C$" and the inductor "$L_C$" that are in series or, equivalently, the capacitor "C" as illustrated in the circuit model 630. The electrical connections (e.g., the connecting wires) can be parasitic and, thus includes parasitic resistors "$R_p$" and parasitic inductors "$L_p$." Such parasitic resistors "$R_p$" and parasitic inductors "$L_p$" can be ignored.

As illustrated with the arrows through the resistor "$R_C$" and the inductor "$L_C$," the counteracting magnetic field changes (e.g., increases) the value of the resistor "$R_C$" and changes (e.g., decreases) the value of the inductor "$L_C$." In an example, the capacitor "C" is predesigned to have a capacitance in the range of one-hundred to three-hundred picofarads. The resistor "$R_C$" is predesigned to have a resistance in the range of one to one-hundred ohms. The inductor "$L_C$" s predesigned to have an inductance in the range of one to one-hundred microhenrys.

Heterodyne downshifting for faster frequency readout is possible. For instance, the sampling rate of the frequency counter may be limited to forty samples per second. If a higher sampling rate is required, the coil voltage can be connected to a frequency mixer, where it gets mixed with a reference signal and downshifted to a lower frequency at 1 kHz. This lower-frequency signal is sampled by an analogto-digital converter, band pass filtered and conditioned by digital signal processing algorithms to recover the resonant frequency. By doing so, a higher sampling rage is possible, such as one higher than two-hundred samples per second.

Figure 7:
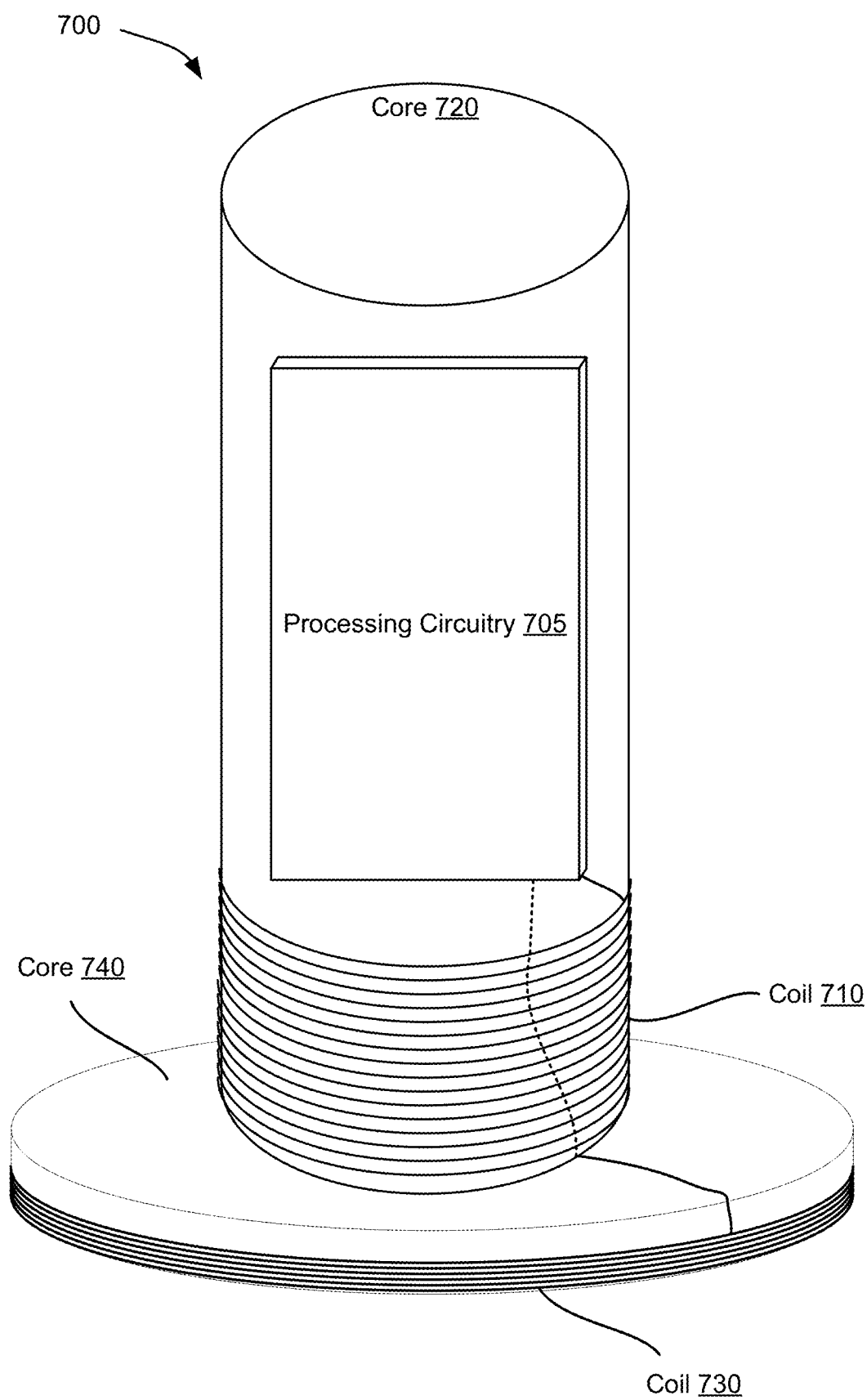
FIG. 7 illustrates examples of components of an inductive damping sensor of a sensor system in accordance with an embodiment.

FIG. 7 illustrates examples of components of an inductive damping sensor 700 of a sensor system in accordance with an embodiment. Here, the inductive damping sensor 700 includes multiple sensors, each of which can be an inductive damping sensor that produces a magnetic field having a particular depth, and collectively have a substantially same resonance frequency.

As illustrated, the inductive damping sensor 700 includes multiple coils, each of which is looped around a different core. Two coils and two cores (e.g., a first coil 710 looped around a first core 720, and a second coil 740 looped around a second core 740) are illustrated in FIG. 7, although a larger number of coils and/or cores are possible. The first core 720 and the second core 700 are attached together. For instance, each of these cores 720 and 740 is a cylindrical core and they are attached at opposite surfaces (e.g., bottom surface of the first core 720 and top surface of the second core 740) such that they are concentric around their opposite surfaces. Alternatively or additionally, the cores can be disposed such as a larger core (e.g., the second core 740) includes a smaller core (e.g., the first core 720) such that their vertical axes are aligned and such that at least a portion of the coils belong to a same plane (e.g., the bottom of the second coil 730 and the bottom of the first coil 710 belong to a same horizontal plane).

In addition, the inductive damping sensor 700 can include a number of processing circuitry electrically coupled with the coils 710 and 730. Although FIG. 7 illustrates a single processing circuitry 705 electrically coupled to the two coils 710 and 730, a different number of processing circuitry is possible. For instance, each coil of the inductive damping sensor 700 can be electrically coupled to an individual processing circuitry. Generally, the processing circuitry 706 includes similar components as the processing circuitry 405 of FIG. 4.

Generally, the size of a coil (e.g., its diameter) and the total number of loops, among other factors, impact the depth of the generated magnetic field. The larger the size is and/or the larger the number of loops, the deeper the magnetic field is. By having multiple coils, each having a specific size and/or specific number of loops, it is possible to detect the health condition of an organ at different depths (optionally, different resonance frequencies can be achieved to detect the health condition at a same depth or different depths).

To illustrate, consider an example of desiring to measure a depth of ten centimeters at a one centimeter resolution. In this case, the inductive damping sensor 700 can include ten coils sized incrementally. As the size increases from one coil to the next, the number of loops decreases to achieve a particular resonance frequency across the ten coils. The smallest coil can have a diameter of about two centimeters and include thirty-five loops. The largest coil can have a diameter of about twelve centimeters and include five loops.

In operation, the inductive damping sensor 700 is placed in proximity of an organ to check whether a conductive fluid is present in the organ and the depth of this fluid. The conductive fluid is within the magnetic field of the third, fourth, and fifth coils, but not the remaining coils. Hence, the measurement data from the different sensors would indicate that the conductive fluid is detected by the third, fourth, and fifth sensors, corresponding to depths of three, four, and five centimeters. Accordingly, it can be concluded that the fluid is present at a depth of three to five centimeters within the organ.

In an example, in addition to using multiple sensors within the inductive damping sensor 700 to measure depth, it may be possible to generate three dimensional (3D) modeling of the target organ (or the volume of conductive fluid within the target organ). In particular, the inductive damping sensor 700 can include one or more pose sensors to measure a pose (e.g., position and orientation) of the inductive damping sensor 700. Such pose sensors can include, for instance, a gyroscope and an accelerometer. By moving the inductive damping sensor 700 in a scanning motion (e.g., around the skull), inductance and resistance measurements are collected in conjunction with position and orientation. The inductance and resistance measurements are used to determine the conductivity of the organ (or fluid), such as the brain (or the blood in the brain), and translate these measurements into a health condition (e.g., the presence of the fluid in the brain). The position and orientation data can be mapped into a coordinate system to generate a 3D model of the brain, where the presence of the fluid is presented in the 3D model to indicate the location of the fluid in the brain.

Figure 8:
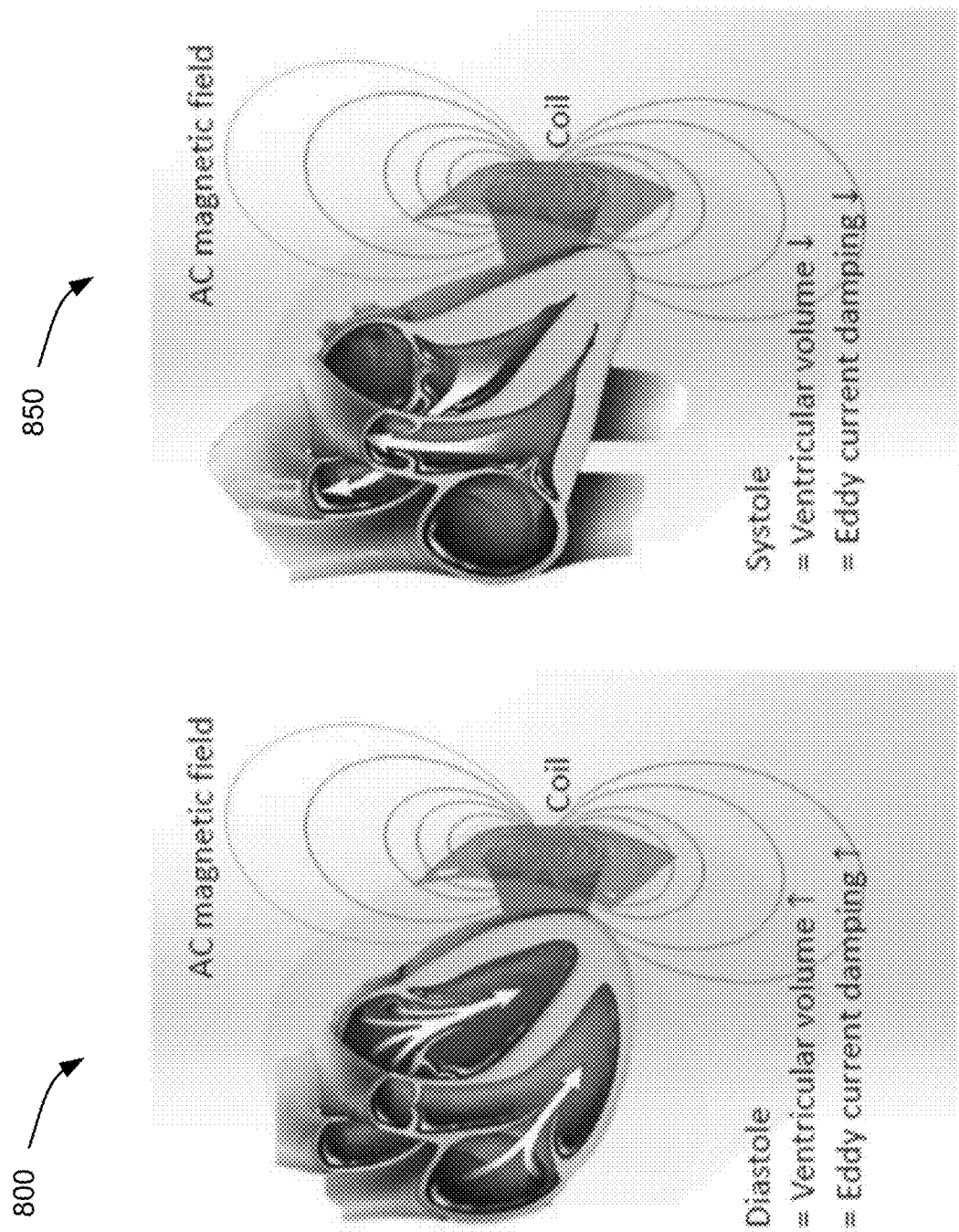
FIG. 8 illustrates examples of associating a heartbeat with a magnetic field of an inductive damping sensor in accordance with an embodiment.

FIG. 8 illustrates examples of associating a heartbeat with a magnetic field of an inductive damping sensor in accordance with an embodiment. Generally, a heart includes a ventricular volume that can contain blood and the volume changes depending on the heartbeat. At diastole 800 (the phase of the heartbeat when the heart muscle relaxes and allows the ventricular volume to fill with blood), the ventricular volume increases, resulting in an increase of the volume of blood. At systole 850 (the phase of the heartbeat when the heart muscle contracts and pumps blood from the ventricular volume into the arteries), the ventricular volume decreases, resulting in a decrease of the volume of blood. As explained in connection with FIG. 5 above, blood has a higher conductivity than the muscle. Accordingly, at diastole 800, the conductivity of the heart filled with blood is relatively high, whereas at systole 800, the conductivity of the heart with the least amount of blood is relatively small.

When an inductive damping sensor is placed in proximity of the heart (e.g., over the left side of the chest) and its magnetic field contains the heart, the eddy current damping changes in the inductive damping sensor (e.g., in the coil of the inductive damping sensor) depending on the diastole 800 and the systole 850. In particular, the eddy current damping increases at the diastole 800 and decreases at the systole 850. Hence, it is possible to monitor the heartbeat by measuring the change in the inductance and/or resistance of the coil. Specifically, the largest decrease to the inductance relative to a predesigned coil inductance (or equivalently the largest increase to the resonant frequency relative to a predesigned coil resonant) and/or the largest increase to the resistance relative to a predesigned coil resistance indicates the diastole 800. Conversely, the largest increase to the inductance (or equivalently the largest decrease to the resonant frequency) and/or the largest decrease to the resistance indicates the systole 850. The time between the peak and valley of the inductance, resonant frequency, and/or resistance can be translated into a pulse rate.

Figure 9:
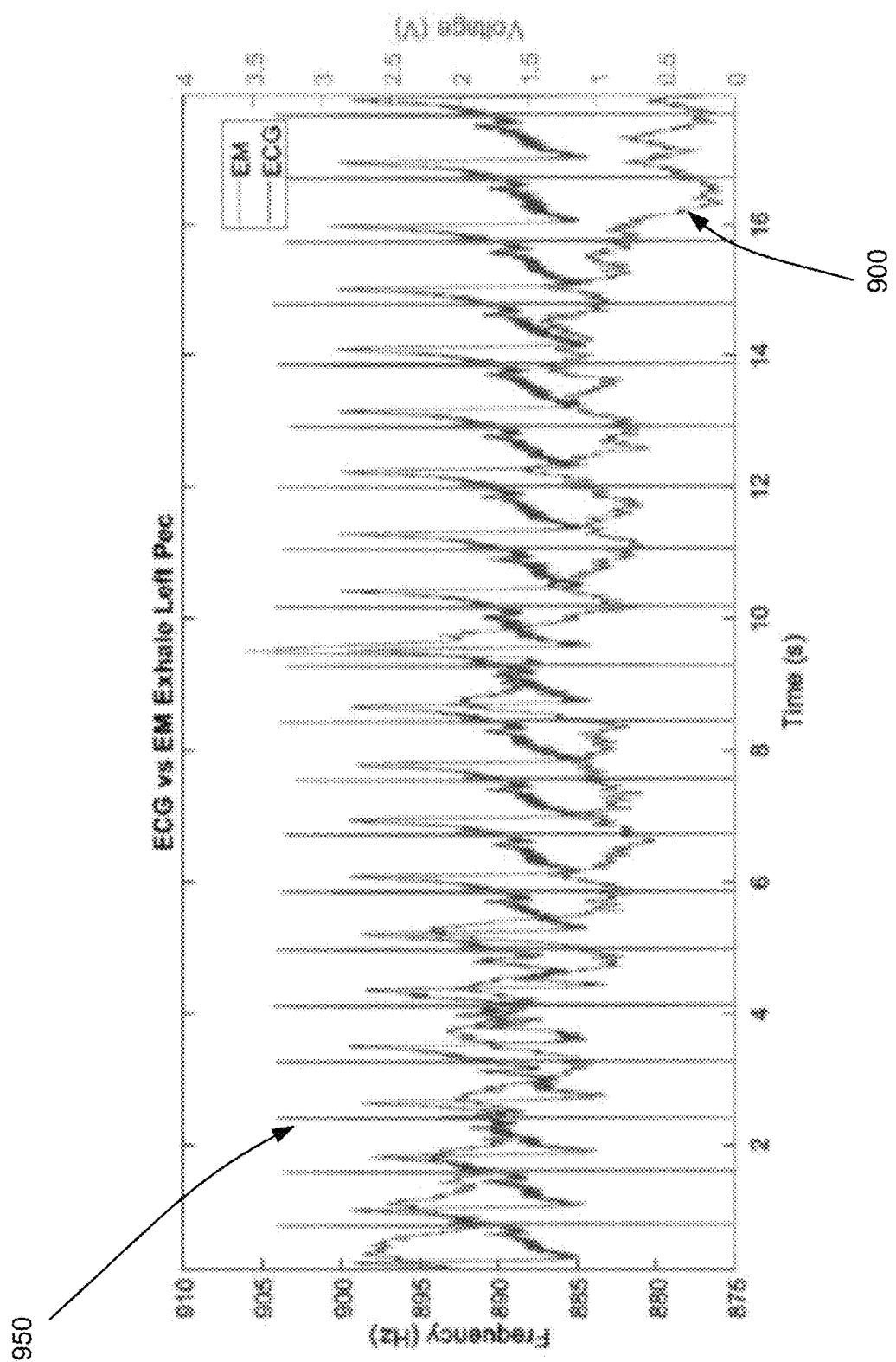
FIG. 9 illustrates examples of measuring a heart rate in accordance with an embodiment.

FIG. 9 illustrates examples of measuring a heart rate in accordance with an embodiment. As illustrated, the heart rate is measured according to two methods. The first method 900 relies on an inductive damping sensor to measure the changes to the resonant frequency of a coil of the inductive damping sensor, as explained in connection with FIG. 8 and illustrated in FIG. 9 with the label EM for electromagnetism.

The second method 950 is a conventional electrocardiography (ECG) method. FIG. 9 compares the outcome of both methods, where the horizontal line is time, the left vertical line is the frequency measurement of the first method 900, and the right vertical line is the voltage measurement of the second method 950.

According to the first method 900, it should be expected that the peak (e.g., largest value) of the resonant frequency would correspond to the diastole and the valley (e.g., the smallest value) of the resonant frequency to correspond to the systole. As can be seen in FIG. 9, such peaks and valleys are observed and match the heart rate measured according to the second method 950. In particular, the resonant frequency can be precisely determined with a 0.7 Hz resolution at 1.5 MHz, while the signal from the heart beat is around 2 Hz to 3 Hz. The waveform of the first method 900 recorded concurrently with the waveform of the second method 950 shows excellent correlation to the conventional ECG method for heart rate detection.

Figure 10:
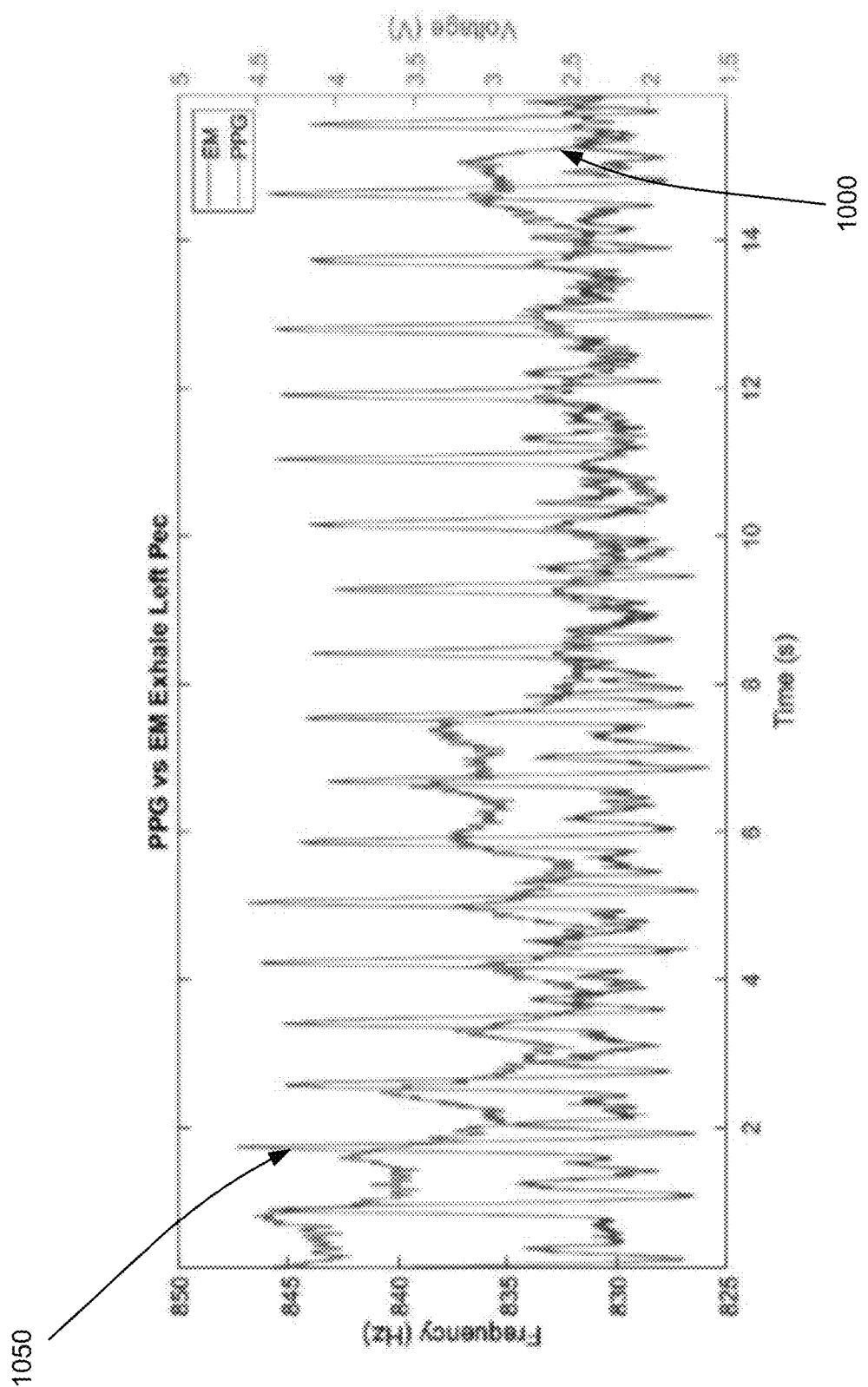
FIG. 10 illustrates other examples of measuring a heart rate in accordance with an embodiment.

FIG. 10 illustrates other examples of measuring a heart rate in accordance with an embodiment. As illustrated, the heart rate is measured according to two methods. The first method 1000 relies on an inductive damping sensor to measure the changes to the resonant frequency of a coil of the inductive damping sensor, as explained in connection with FIG. 8 and illustrated in FIG. 10 with the label EM for electromagnetism. The second method 1050 is a conventional photoplethysmography (PPG) method. FIG. 10 compares the outcome of both methods, where the horizontal line is time, the left vertical line is the frequency measurement of the first method 1000, and the right vertical line is the voltage measurement of the second method 1050.

According to the first method 1000, it should be expected that the peak (e.g., largest value) of the resonant frequency would correspond to the diastole and the valley (e.g., the smallest value) of the resonant frequency to correspond to the systole. As can be seen in FIG. 10, such peaks and valleys are observed and match the heart rate measured according to the second method 1050. In particular, the resonant frequency can be precisely determined with a 0.7 Hz resolution at 1.5 MHz, while the signal from the heart beat is around 2 Hz to 3 Hz. The waveform of the first method 1000 recorded concurrently with the waveform of the second method 1050 shows excellent correlation to the conventional PPG method for heart rate detection.

Figure 11:
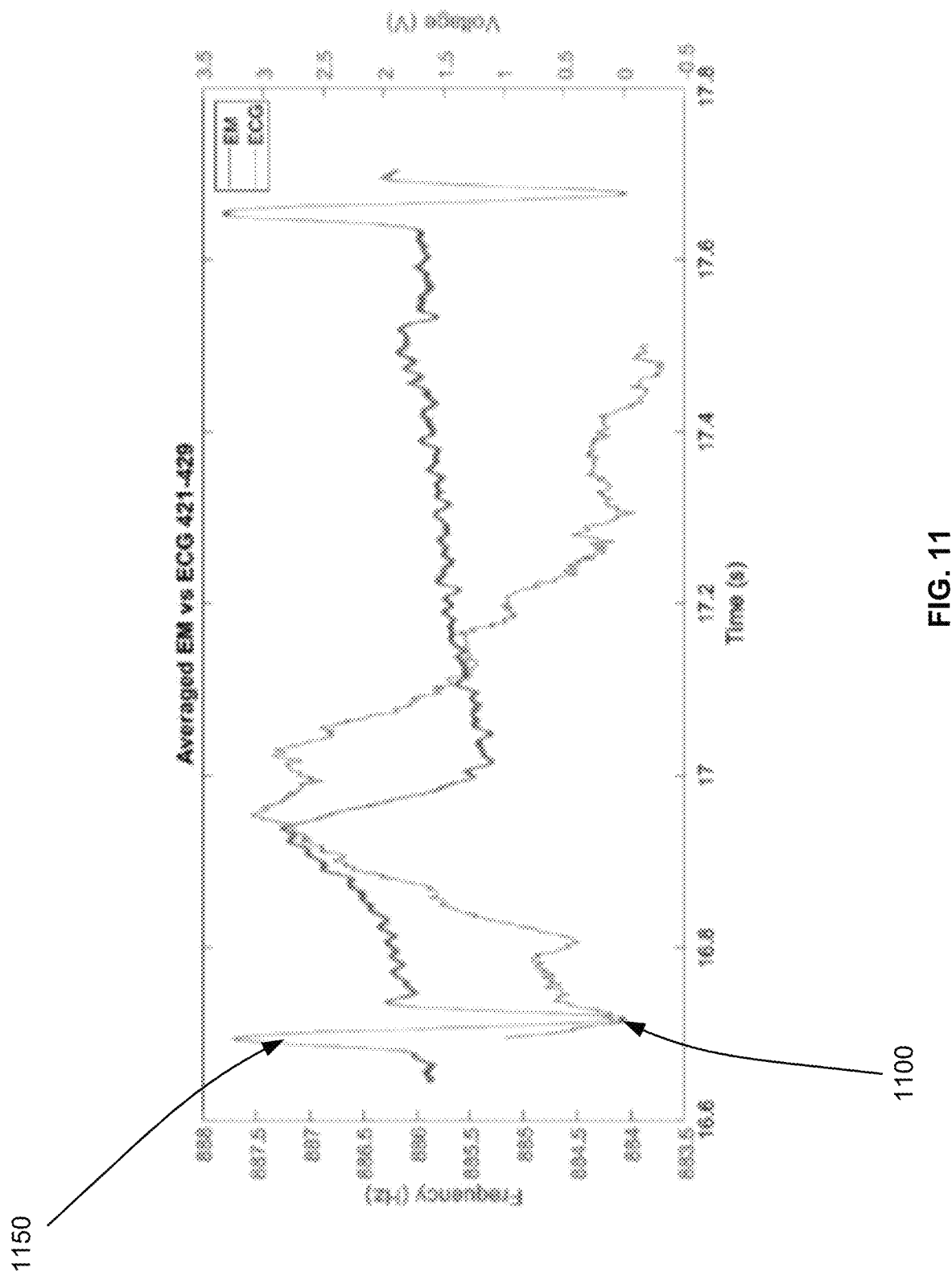
FIG. 11 illustrates examples of associating a heartbeat with a heart ejection fraction in accordance with an embodiment.

FIG. 11 illustrates examples of associating a heartbeat with a heart ejection fraction in accordance with an embodiment. In addition to measuring a heart rate, the ejection fraction of the heart can be measured based on the inductance and/or resistance of the coil (or the changes thereto) of an inductive damping sensor. Ejection fraction refers to the amount, or percentage, of blood that is pumped (or ejected) out of the ventricles with each contraction.

To estimate the ejection fraction, the shape of the heart can be approximated by an ellipsoid. The ejection fraction can be estimates as a function of the stroke volume. In turn, the stroke volume can be estimated from the relative frequency shift between the diastole and the systole. Through empirical data and experimentation, the frequency shift can be associated with the stroke volume. For instance, and as illustrated in FIG. 11, ex vivo measurement shows that a frequency shift around 3 Hz corresponds to a stroke volume of about 67 mL. Such experiments can be performed for different subjects to build a model that associates frequency shifts (or similarly inductance change and/or resistance change) with corresponding stroke volumes.

In FIG. 11, a heartbeat is measured according to two methods. The first method 1100 relies on the inductive damping sensor to measure the changes to the resonant frequency of a coil of the inductive damping sensor, as explained in connection with FIG. 8 and illustrated in FIG. 11 with the label EM for electromagnetism. The second method 1150 is a conventional ECG method. FIG. 11 compares the outcome of both methods, where the horizontal line is time, the left vertical line is the frequency measurement of the first method 1200, and the right vertical line is the voltage measurement of the second method 1150. As can be seen, the frequency changes from about 884 Hz to about 887 Hz (e.g., a frequency shift of 3 Hz). The peak and valley of the heart beat correspond to the peak and valley of the ECG method, thereby validating the correctness of the measurements of the first method 1100.

Based on FIGS. 8-11, an inductive damping sensor can be used for the detection of a heartbeat, a heart rate, and/or an ejection fraction. In an example, the inductive damping sensor includes a coil that has a predesigned inductance, a predesigned resonant frequency, and a predesigned resistance. For the sake of clarity, the use of the resonant frequency is described. However, the description similarly applies to the use of the inductance and resistance. It may suffice to use one of the three electrical properties, although it is possible to use a combination of two of them or to use all three of them.

Measurement data are generated by the inductive damping sensor and indicate values of measured resonant frequency of the coil over time. The values change relative to the predesigned resonant frequency because of the volume of the blood in the heart. The measured values can be plotted over time. A pair of a peak adjacent with a valley indicates the heartbeat. Time intervals between the pairs indicate the heart rate. The amount of frequency change between a peak and a valley can be determined from the measurement data and is pre-associated with a stroke volume that indicates the ejection fraction.

Hence, a health diagnosis application for detecting a health condition of a heart (the detection of a heartbeat, a heart rate, and/or an ejection fraction) can be developed. The health diagnosis application stores pre-associations between peak-to-valley frequency changes and corresponding ejection fractions. The health diagnosis application analyzes the measurement data to determine the peaks and valleys and their times and can detect the heartbeat based on the presence of the peaks and valleys, compute the heart rate from their times, and estimate the ejection rate by determining a peak-to-valley frequency change (e.g., an average over time) and looking up the pre-associations.

Figure 12:
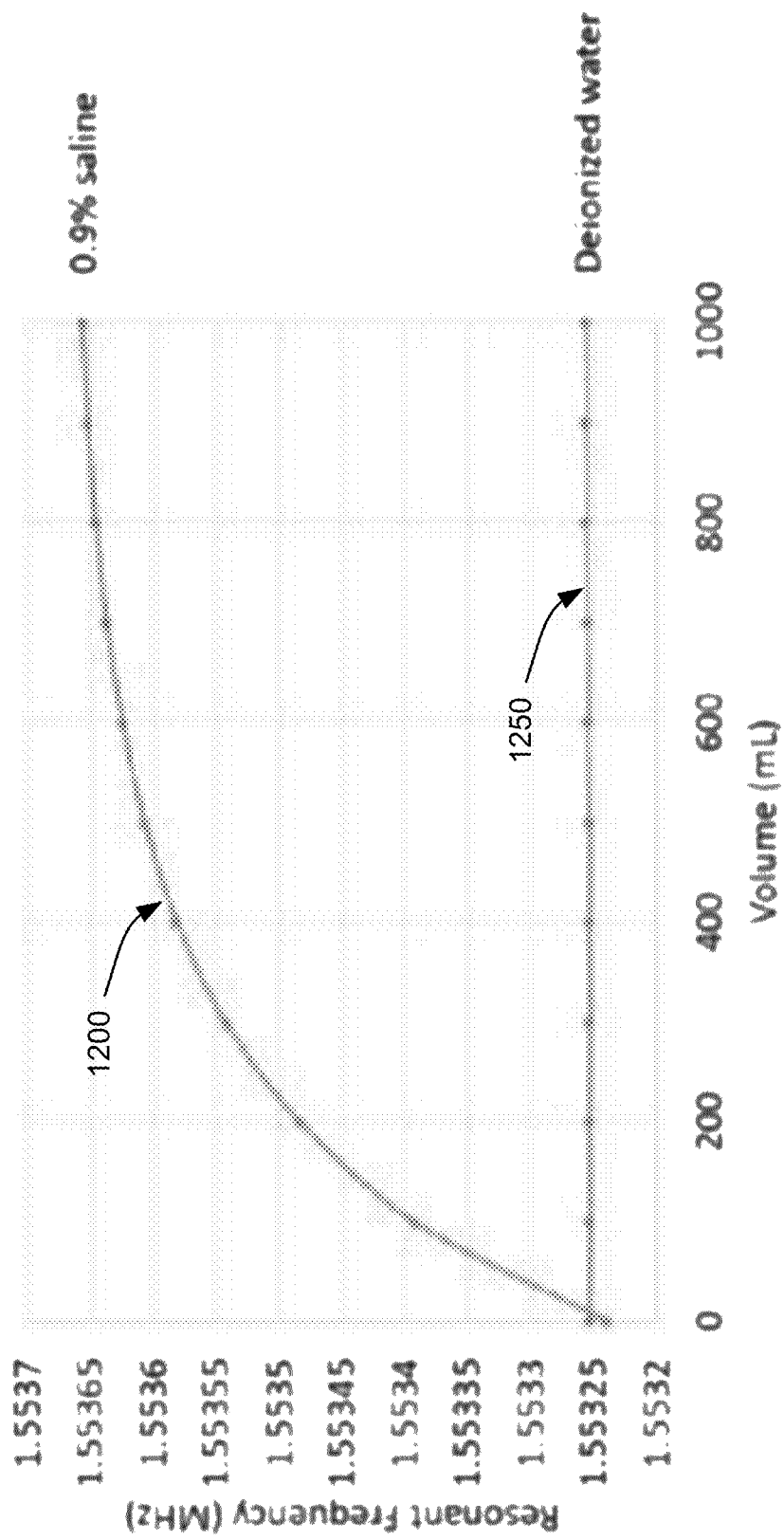
FIG. 12 illustrates an example of a proof of concept for edema detection in accordance with an embodiment.

FIG. 12 illustrates an example of a proof of concept for edema detection in accordance with an embodiment. Over 900,000 new cases of heart failure are diagnosed per year. One of the early warning signs is buildup of excess fluid in body tissues, also known as edema. This symptom can occur in lungs, four limbs, brain or abdomen.

There are two existing products to diagnose skin edema, spring tape measure and optoelectronic volumetry. However, the existing products have several drawbacks including human intervention and lack of portability. The inductive damping sensor of the present disclosure allows easy and automated point-of-care diagnosis and sends out early warnings to the subject who likely needs immediate clinical interventions.

As illustrated in FIG. 12, the horizontal line illustrates a volume of a fluid and a vertical line illustrates a resonant frequency of the coil of the inductive damping sensor in proximity of the volume. Two fluids are used: one that includes a 0.9% saline solution, similar to what would be expected in edema, and one that includes deionized water. The 0.9% saline solution is highly conductive (e.g., as shown in FIG. 5), whereas the deionized water is not.

The inductive damping sensor is placed next to the 0.9% saline solution. The volume is increased at 100 mL increments and measurement of the coil's resonant frequency is performed at each volume level of the 0.9% saline solution. Similarly, the inductive damping sensor is placed next to the deionized water. The volume is increased at 100 mL increments and measurement of the coil's resonant frequency is performed at each volume level of the deionized water. The measurements are plotted, where curve 1200 corresponds to the 0.9% solution and curve 1250 corresponds to the deionized water.

As can be seen from the plots, an increase to the volume of the 0.9% solution leads generally to an increase of the resonant frequency. However, the resonant frequency of the coil does not change with an increase to the volume of the deionized water. Such measurements prove that it is possible to use inductive damping sensor to detect edema, whereby an increase to the resonant frequency indicates the presence of a saline fluid, and whereby the higher the resonant frequency is relative to a predesigned resonant frequency, the larger the volume of the saline solution is.

Figure 13:
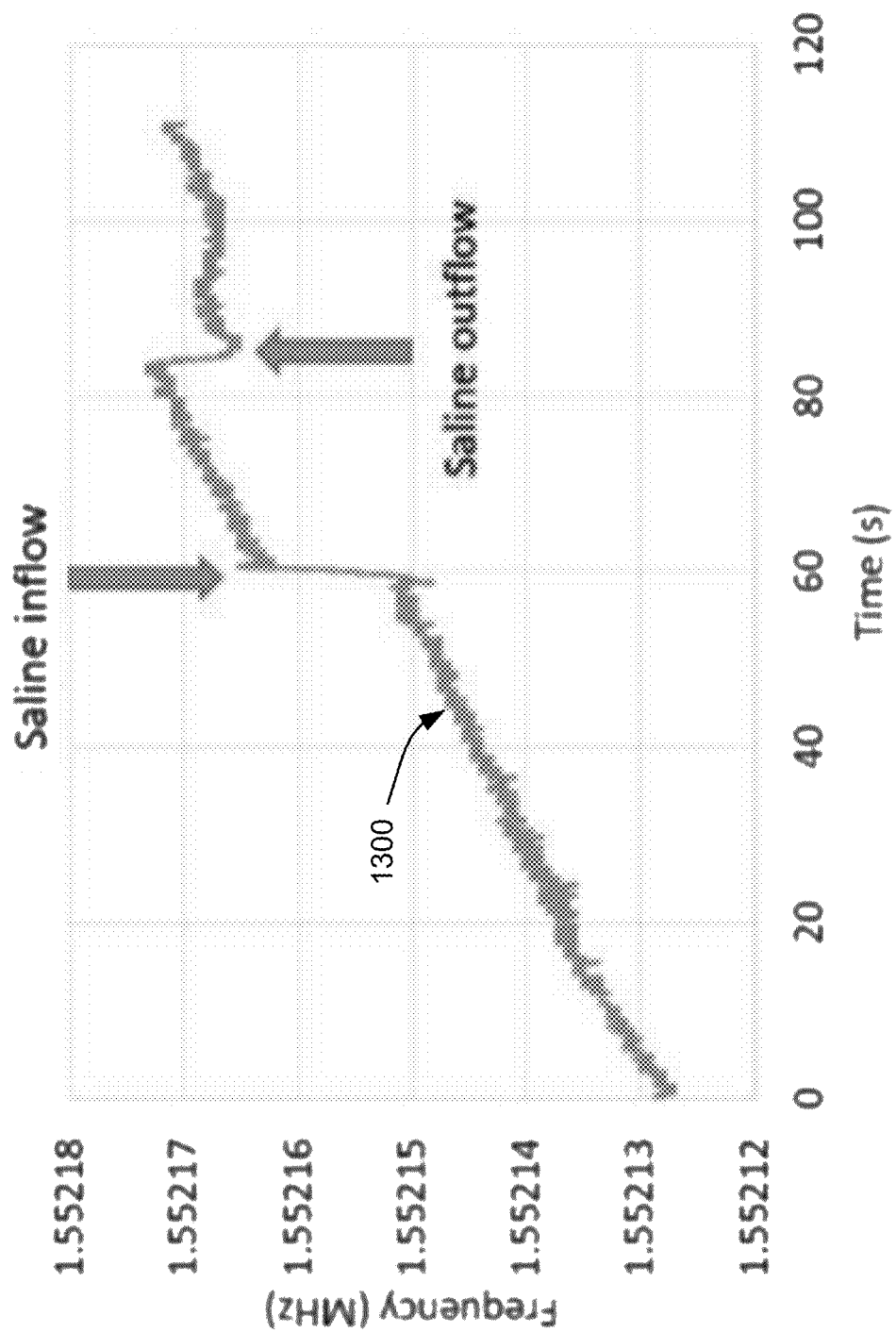
FIG. 13 illustrates another example of a proof of concept for edema detection in accordance with an embodiment.

FIG. 13 illustrates another example of a proof of concept for edema detection in accordance with an embodiment. Here, a volume containing a 0.9% saline solution is increased over time, where the volume is set to 100 mL at the start and is increased to 200 mL at the end. At a particular time (illustrated at about sixty seconds in FIG. 13), the inflow of the 0.9% saline solution is increased significantly and momentarily. At another time (illustrated at about eighty-two seconds in FIG. 13), an outflow of the 0.9% saline solution occurs significantly and momentarily. An inductive damping sensor is placed next to the 0.9% solution and measurements of the resonant frequency are performed over time. The frequency measurements are plotted as curve 1300, where the horizontal line corresponds to time and the vertical line corresponds to the frequency. As can be seen, the resonant frequency increases over time and steps up at the particular time when the inflow is increased significantly and momentarily and steps down at the other when the outflow occurs significantly and momentarily. Here also, the measurements prove that it is possible to use an inductive damping sensor to detect edema.

In an example, a health diagnosis application for detecting an edema health condition (e.g., presence of edema, volume of saline fluid causing the edema) of an organ (e.g., lungs, limbs, brain, abdomen) can be developed. An example of using the resonant frequency of the coil is described. However, the health diagnosis application can similarly analyze the inductance and/or resistance of the coil. The health diagnosis application stores an expected resonant frequency given a known conductivity of a target organ that is healthy (e.g., lungs, limbs, brain, or abdomen that do not suffer from edema). The health diagnosis application also stores pre-associations between values of the resonant frequency and volumes of a saline solution in the target organ, where these pre-associations can be developed through empirical data and experimentation. In operation, the health diagnosis application receives measurement data of the inductive damping sensor, where the measurement data indicates the measured resonant frequency. The health diagnosis application compares the measured resonant frequency to the expected resonant frequency. If the difference between the two is larger than a predefined threshold (e.g., five percent), the health diagnosis application detects that edema is present. In addition, the health diagnosis application uses the measured reasoned frequency to look up the pre-associations and estimate the volume of the present saline solution.

Figure 14:
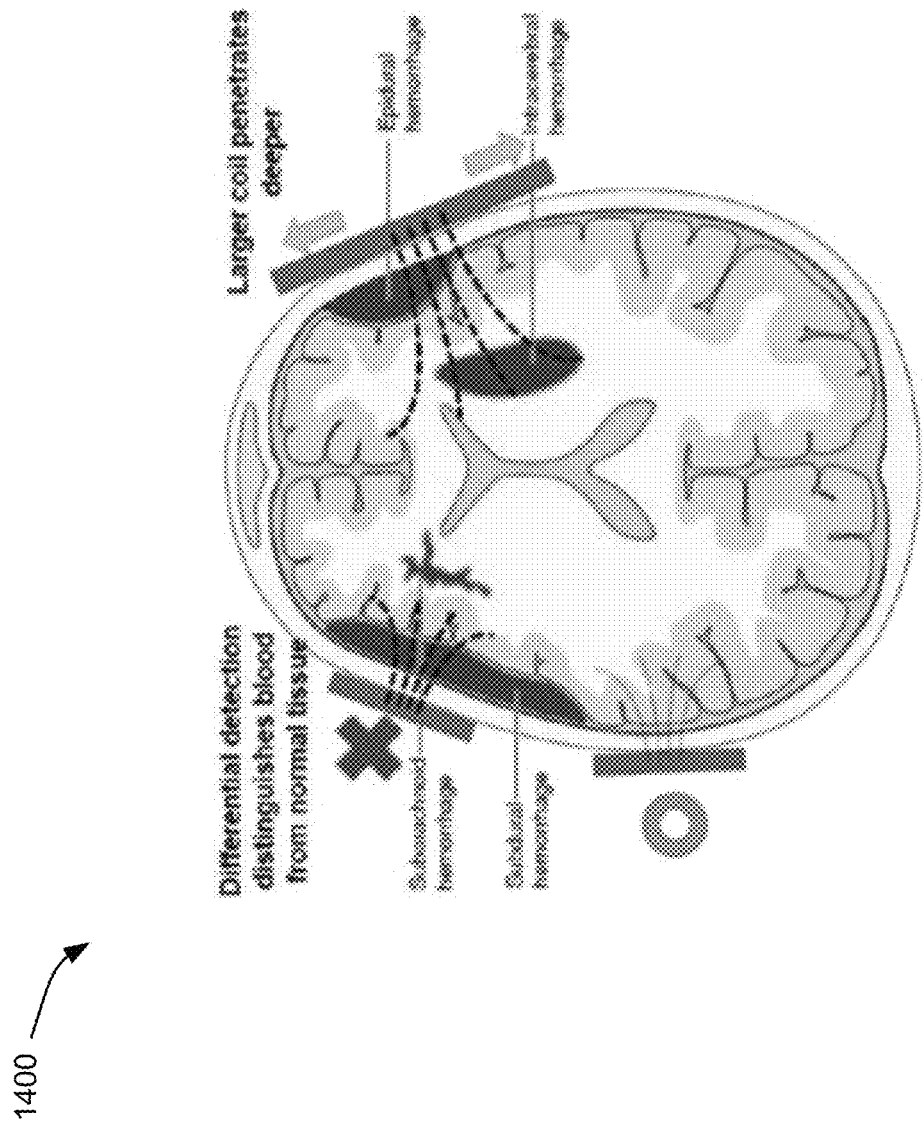
FIG. 14 illustrates examples of brain diagnosis in accordance with an embodiment.

FIG. 14 illustrates examples of brain diagnosis in accordance with an embodiment. In particular, the inductive damping sensor of the present disclosure is usable to detect intracranial hemorrhage, hemorrhagic stroke, and ischemic stroke. The detection of each of these conditions is further described herein below. Generally, the brain has a known conductivity, as described in connection with FIG. 5. An increase to the conductivity of the brain can be due to the presence of additional blood and would result in an increase to the conductivity because of the higher conductivity of blood. A decrease to the conductivity of the brain can be due to a restriction on the flow of the blood to the brain. In other words, a healthy brain has a known conductivity, and a deterioration of the brain health can be detected from change in the conductivity. By placing an inductive damping sensor next to the brain, one or more electrical properties (e.g., inductance, resonant frequency, and/or resistance) of the coil can be measured, where the value(s) of the electrical property(ies) depends on the conductivity of the brain. Hence, the measured electrical property(ies) of the coil can be associated with the health condition of the brain.

Intracranial hemorrhage can occur in all compartments within the skull. Intracerebral hematomas occur either spontaneously or traumatically within the brain tissue, whereas subdural and epidural hematomas are often associated with traumatic head injury. The state-of-the-art noninvasive diagnostic tool is based on near infrared spectroscopy, which distinguishes the blood from the normal brain tissue. However, the optical penetration depth is limited to about one centimeter. Hence, deeper lesions like intracerebral hemorrhage are beyond such detection capability.

In contrast, inductive damping sensors of the present disclosure resolve this limited capability issue. In particular, an inductive damping sensor can detect intracranial hemorrhage based on the measured electrical property(ies) of the coil. For the sake of clarity, the use of the resonant frequency is described. However, the description similarly applies to the use of the inductance and resistance. It may suffice to use one of the three electrical properties, although it is possible to use a combination of two of them or to use all three of them.

The conductivity of a healthy brain is known. The coil has a predesigned resonant frequency. When the inductive damping sensor is placed next to the healthy brain, the resonant frequency is expected to change to a certain value given the known conductivity. If that value is measured (e.g., the difference between the measured resonant frequency and the expected resonant frequency is within a threshold, such as five percent), the brain is detected to be healthy. However, an increase to the value (e.g., a measured resonant frequency larger than what is expected, such that the difference is greater than the threshold) indicates the presence of the intracranial hemorrhage within the brain. In this case, the location over the brain where the resonant frequency is measured indicates a region in the brain where the intracranial hemorrhage is present, where the region is below the location. The depth of the region depends on the magnetic field depth generated from the coil. Here also, through empirical data and experimentation, pre-associations can be generated between the measured resonant frequency and the volume of blood causing the intracranial hemorrhage.

As also explained herein above, the depth of the magnetic sensor can depend on the size of the coil and/or the number of loops. Hence, for detection of hemorrhage located deep in the brain, a large size coil can be used to allow deeper magnetic field penetration.

As illustrated in connection with FIG. 7, it is possible to use an inductive damping sensor that includes multiple coils providing different depth resolutions. The combination of different size coils can profile the brain from epidural space (higher sensitivity) to the ventricular space.

Accordingly, and as shown in FIG. 14, different uses 1400 of an inductive damping sensor are possible. In one use, a single inductive damping sensor can be used for detecting intracranial hemorrhage given the difference between the conductivity of the healthy brain tissue and blood. An inductive damping sensor with a larger coil can be used for the detection of deeper intracranial hemorrhage. In addition, a multi-coil inductive damping sensor can be used to determine the depth (e.g., start and end) of the intracranial hemorrhage. By scanning the brain in different directions, it is possible to generate an image of the intracranial hemorrhage, where the image can show the depth.

There are two types of strokes. The first is hemorrhagic, in which a vessel ruptures in the brain and leads to excessive bleeding, which can compress areas of the brain and prevent adequate perfusion, leading to cell death. The second is ischemic, in which an embolus, thrombus, or plaque block a vessel and lead to decreased blood flow and cell death. These two types of strokes are extremely time dependent and have vastly different treatments, and if a hemorrhagic stroke is mistaken for an ischemic stroke and treated as such, the subject is likely to bleed out.

The current diagnosis techniques for hemorrhagic and ischemic strokes include computerized tomography (CT) scans and MRI imaging of the head, both of which are expensive and timely. Also, CT scans use radiation to image the brain, and studies have shown that up to 2% of the cancers that arise each year could be due to CT scan radiation.

In comparison, the inductive damping sensor of the present disclosure allows quick and simple detection of the hemorrhagic and ischemic strokes, while also differentiating between the two strokes because the hemorrhagic stroke increases the conductivity of the brain (and hence, decreases the inductance and increases the resonant frequency and resistance of the coil) due to increased blood, and because the ischemic stroke decreases the conductivity of the brain (and hence, increases the inductance and decreases the resonant frequency and resistance of the coil). The inductive damping sensor has an improved temporal resolution that does not involve harmful radiation.

In an example, the conductivity of the brain is known. The coil has a predesigned resonant frequency. A particular value of the resonant frequency is expected when the coil is placed in proximity of the heart. However, if the measured resonant frequency is larger than the expected value by a first threshold, the hemorrhagic stroke is detected. If the measured resonant frequency is smaller than the expected value by a second threshold, the ischemic stroke is detected. If the difference between the measured resonant frequency and the expected value is between the second threshold and the first threshold, no stroke is detected.

In an example, a health diagnosis application for detecting brain health condition (e.g., intracranial hemorrhage, hemorrhagic stroke, ischemic stroke, volume of hemorrhage, and depth of hemorrhage and/or stroke) can be developed. An example of using the resonant frequency of the coil is described. However, the health diagnosis application can similarly analyze the inductance and/or resistance of the coil. The health diagnosis application stores an expected resonant frequency given a known conductivity of a healthy brain (e.g., a brain that does not suffer from intracranial hemorrhage, hemorrhagic stroke, ischemic stroke). The health diagnosis application also stores pre-associations between values of the resonant frequency and volumes of blood in hemorrhage region within the brain, where these pre-associations can be developed through empirical data and experimentation. In operation, the health diagnosis application receives measurement data of the inductive damping sensor, where the measurement data indicates the measured resonant frequency. The health diagnosis application compares the measured resonant frequency to the expected resonant frequency. If the difference between the two is larger than a first threshold (e.g., plus five percent), the health diagnosis application detects that intracranial hemorrhage is present and that the hemorrhage corresponds to a hemorrhagic stroke. In addition, the health diagnosis application uses the measured reasoned frequency to look-up the pre-associations and estimate the volume of the blood. If the difference between the two is smaller than a second threshold (e.g., minus five percent), the health diagnosis application detects an ischemic stroke. In addition, the health diagnosis application stores a value that indicates the depth of the magnetic field. When a hemorrhagic stroke or an ischemic stroke is detected, the health diagnosis application can also output a depth of the stroke, where the depth corresponds to the stored value. In an example, multiple coils are used, each of which has a different depth penetration. In this example, the health diagnosis application stores different values for the different depths. Measurement data is generated for each coil and is stored with identifiers of the corresponding coil (e.g., "measurement data A from coil A", "measurement data B from coil B," etc.). The health diagnosis application analyzes the measurement data corresponding to each coil as described herein above and determines the identifiers of the coils where the hemorrhage or stroke was detected. The identifiers are used to look up the corresponding depth values of the coils to then return a depth range (e.g., start and end) of the hemorrhage or stroke.

Figure 15:
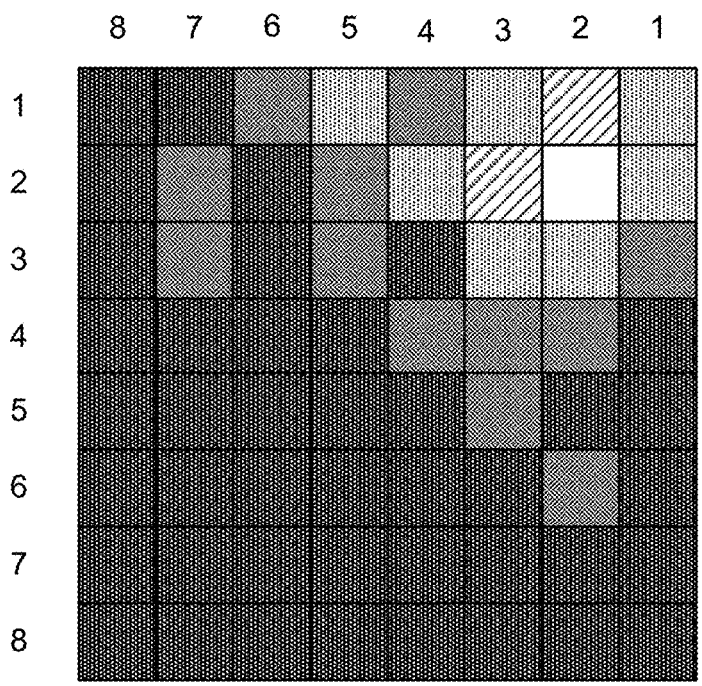
FIG. 15 illustrates an example of mapping a brain in accordance with an embodiment.
Figure 15:
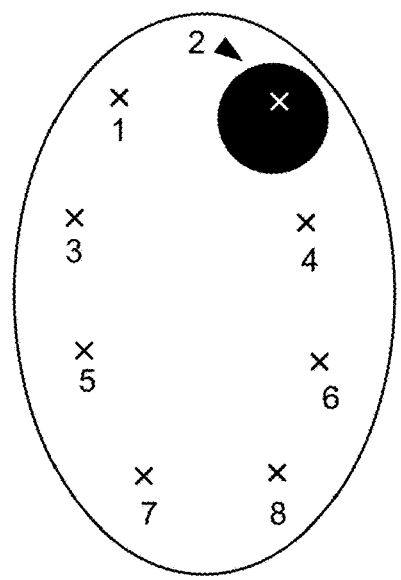

FIG. 15 illustrates an example of mapping a brain in accordance with an embodiment. In an example, an inductive damping sensor of the present disclosure is usable to generate a map 1500 of a brain 1550, where the map 1500 indicates a location of hemorrhage or ischemia in the brain 1550.

The inductive damping sensor can be placed over the skull and moved in a scanning motion. One or more electrical properties of the coil of the inductive damping sensor (e.g., impedance, resonant frequency, and/or resistance) can be measured along with the scanning motion. The measurement data can be stored in conjunction with location data of the inductive damping sensor relative to the skull. The location data and measurement data are used to generate the map 1500, whereby the map shows the measured electrical property(ies) and the various locations.

Different techniques are usable to generate the location data. In one example, tubing is attached to the skull (FIG. 15 illustrates eight tubes with "X" marks). Each tube can be a proximity sensor or a certain type of sensor that detects the presence of the inductive damping sensor over it. The tubes are attached to known locations on the skull. The inductive damping sensor is moved between tubes and the motion is detected (e.g., from tube one to tube two, from tube two to tube four, etc.). In parallel to collecting measurements of the electrical property(ies), the motion is detected and stored as the location data.

In another technique, the inductive damping sensor includes one or more positioning sensors (e.g., a gyroscope and/or an accelerometer). The positioning sensor(s) tracks the pose of the inductive damping sensor (e.g., position and orientation). In parallel to collecting measurements of the electrical property(ies), the pose data is detected and stored as the location data.

In FIG. 15, an illustration of using the first location data technique is described. In particular, an eight by eight map 1500 is generated by imaging a brain having a volume of blood under tubing (2). Each cell in the map corresponds to a motion between or over a tubing. For instance, cell (1,1) corresponds to the inductive damping sensor being over tubing (1). Cell (1,2) corresponds to moving the inductive damping sensor between tubing (1) and tubing (2). And cell (2,2) corresponds to the inductive damping sensor being over tubing (2). The shading of each cell indicates the associated brain conductivity (or equivalently the associated electrical property(ies) of the coil). No shading indicates the highest level of conductivity (e.g., the presence of hemorrhagic blood). The more solid the shading becomes, the lower the conductivity is.

As shown in the map 1500, cell (2,2) is not shaded indicating the highest level of conductivity. This high conductivity corresponds in fact to the location of the volume of blood in the brain (e.g., in the region under tubing (2)). Neighboring cells have some shading and further cells have more solid shading. For instance cell (2,4) has some light shading (shown with the oblique lines) indicating that as the inductive damping sensor is moved away from tubing (2) to tubing (4) the conductivity decreases but is still higher than the typical conductivity of a healthy brain. In other words, the volume of blood extends to a particular point between tube (2) and tube (4).

In an example, a health diagnosis application can generate a map of a brain, similar to the map 1500. The health diagnosis application receives measurement data from the inductive damping sensor and location data from sensors attached to the brain or one or more positioning sensors of the inductive damping sensor. The health diagnosis application compares the measurement data to known data about a healthy brain (e.g., as described herein above in connection with FIG. 14) and detects the brain health conditions at the various locations corresponding to the location data. A graphical presentation scheme (e.g., coloring, shading, etc.) can be used to present the health conditions and the locations.

In addition to the above detection, an inductive damping sensor of the present disclosure is usable for bladder monitoring, fatty liver detection, respiratory rate measurement, and vein and/or artery detection. Each of these uses is described herein next.

Monitoring the urine volume in a bladder is important for elderly or post-surgery patients in bed, who have limited ability to move themselves around. Prolonged accumulation of urine in the bladder can cause infection in the urinary system. In clinics, bladder volume can be estimated by taking the transverse and longitudinal ultrasonic scans.

As described herein in connection with FIG. 5, urine has a relatively high conductivity. Similar to heart stroke volume estimation, the inductance damping sensor measures the frequency shift caused by the accumulation of urine. A health diagnosis application can compute the urine volume from the urine conductivity and bladder geometry.

Hence, the health diagnosis application for bladder monitoring can be developed. The use of resonant frequency is described, although the inductance and resistance of the coil can be similarly used for the bladder monitoring. The health diagnosis application stores pre-associations between peak-to-valley frequency changes and urine volumes. Such pre-associations can be developed through empirical data and experimentation. The health diagnosis application analyzes the measurement data to determine an average of peak-to-valley changes over a predefined time duration (e.g., ten minutes) and estimate the urine volume by using this average to look up the pre-associations.

Fatty liver, medically known as hepatic steatosis or steatohepatitis, can be a result of illness or diet. This condition results in a change in composition of the liver from normal tissue to fatty tissue and can quickly result in liver failure if it is not detected. The inductive damping sensor can be used to detect the conductivity differences between normal liver tissue and fat tissues, and enables diagnosing hepatic steatosis efficiently and non-invasively with no use of radiation or contrast dyes.

A health diagnosis application for fatty liver detection can be developed. The use of resonant frequency is described, although the inductance and resistance of the coil can be similarly used for the fatty liver detection. The health diagnosis application stores an expected resonant frequency given a known conductivity of a healthy liver. In operation, the health diagnosis application receives measurement data of the inductive damping sensor, where the measurement data indicates the measured resonant frequency. The health diagnosis application compares the measured resonant frequency to the expected resonant frequency. If the difference between the two is larger than a predefined threshold (e.g., five percent), the health diagnosis application detects that hepatic steatosis is present.

The respiratory rate corresponds to the flow of blood within the lungs and the contraction and relaxing of the lungs. Hence, the blood flow and lung movement alters the conductivity of the lungs. By placing the inductive damping sensor in proximity to the lungs (e.g., over the chest), it is possible to monitor the change to the conductivity given the association with the change to the impedance, resonant frequency, and/or resistance of the coil of the inductive damping sensor. Here, similarly to the detecting of a heart pulse rate, an application for detecting the respiratory rate can be developed. The use of resonant frequency is described, although the inductance and resistance of the coil can be similarly used for the fatty liver detection.

The health diagnosis application analyzes the measurement data to determine the peaks and valleys and their times and can detect respiration based on the presence of the peaks and valleys. The health diagnosis application also computes the respiratory rate from their times.

Veins and arteries carry blood and, hence, are more conductive than neighboring tissues. To detect a vein (e.g., in the art for drawing blood) or, similarly, an artery, the impedance damping sensor can be used given the difference between conductivity of the vein (or artery) and the conductivity of the neighboring tissue.

A health diagnosis application for vein and/or artery detection can be developed. The use of resonant frequency is described, although the inductance and resistance of the coil can be similarly used for the fatty liver detection. The health diagnosis application stores an expected resonant frequency given a known conductivity of a vein and/or artery. In operation, the health diagnosis application receives measurement data of the inductive damping sensor, where the measurement data indicates the measured resonant frequency. The health diagnosis application compares the measured resonant frequency to the expected resonant frequency. If the difference between the two is smaller than a predefined threshold (e.g., five percent), the health diagnosis application detects the presence of the vein and/or artery at the location of the measurements.

Figure 16:
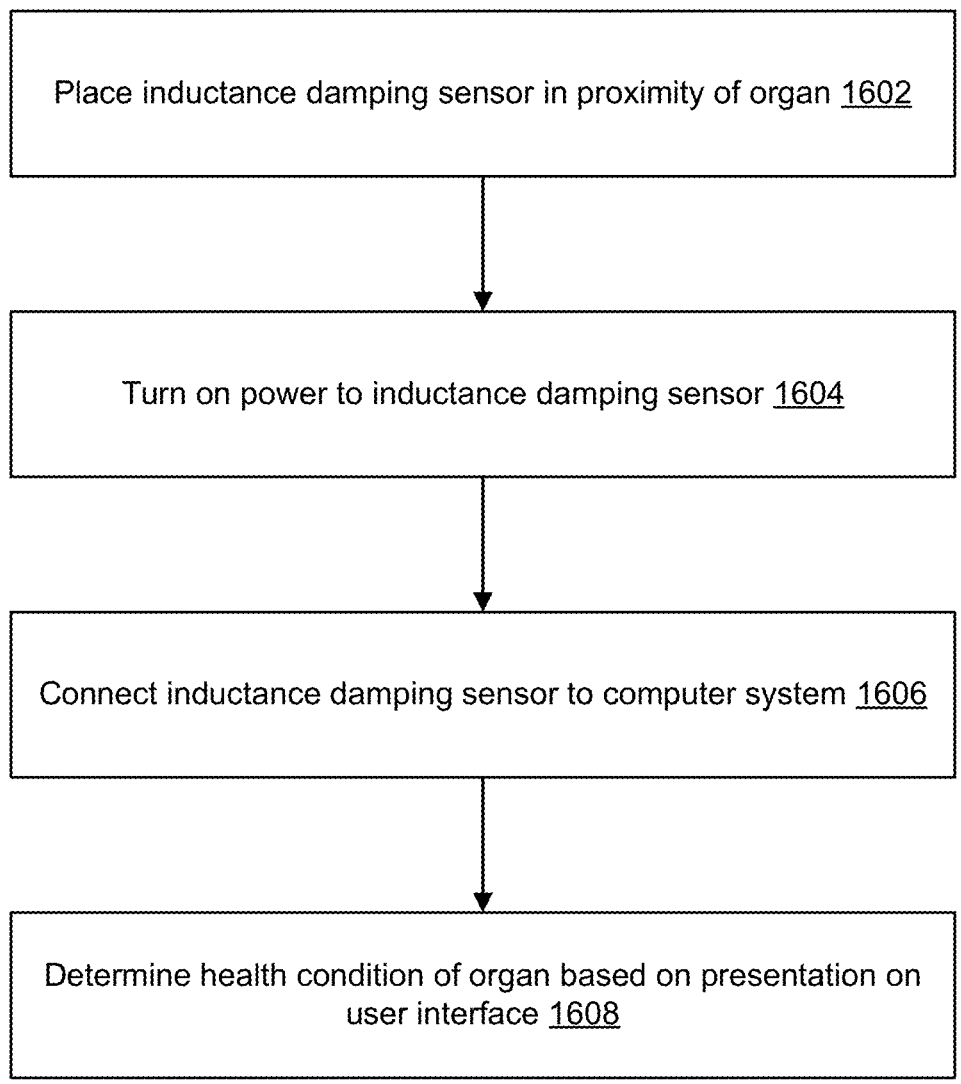
FIG. 16 illustrates an example of a flow for using a sensor system for health diagnosis in accordance with an embodiment.

FIG. 16 illustrates an example of a flow for using a sensor system for health diagnosis in accordance with an embodiment. The sensor system can be used by an operator, where the operator can be a physician or a subject (e.g., a patient). The sensor system includes an inductive damping sensor and a computer system that may be separate from each other or integrated with each other. Although the operations of the flow of FIG. 16 are described in a particular order, the operations can be re-arranged in a different order and one or more of the operations can be skipped or omitted.

In an example, the flow of FIG. 16 starts at operation 1602, where the operator places the inductance damping sensor in proximity of an organ. For instance, the inductance damping sensor has a coil with a predesigned depth penetration such that the magnetic field can contain the organ (e.g., heart, brain, lungs, abdomen, limbs, etc.).

In an example, operation 1604 follows operation 1602. At operation 1604, the operator turns on power to the inductance damping sensor 1604. For instance, if the inductance damping sensor includes an internal power source, the operator switches this power source on. If an external power source is needed, the operator connects the external power source to the inductance damping sensor.

In an example, operation 1606 follows operation 1604. At operation 1606, the operator connects the inductance damping sensor to the computer system. This operation may be skipped when the inductance damping sensor and the computer system are integrated. Connecting the two can be carried via a wire (e.g., a USB wired connection) or wirelessly (e.g., BLUETOOTH pairing, WI-FI connection, etc.).

In an example, operation 1608 follows operation 1606. At operation 1608, the operator determines a health condition of the organ based a presentation on a user interface. For instance, the computer system executes a health diagnosis application and receives measurement data from the inductive damping sensor. The health diagnosis application analyzes the data to detect the health condition and presents the health condition and/or the data on a user interface of the computer system.

Figure 17:
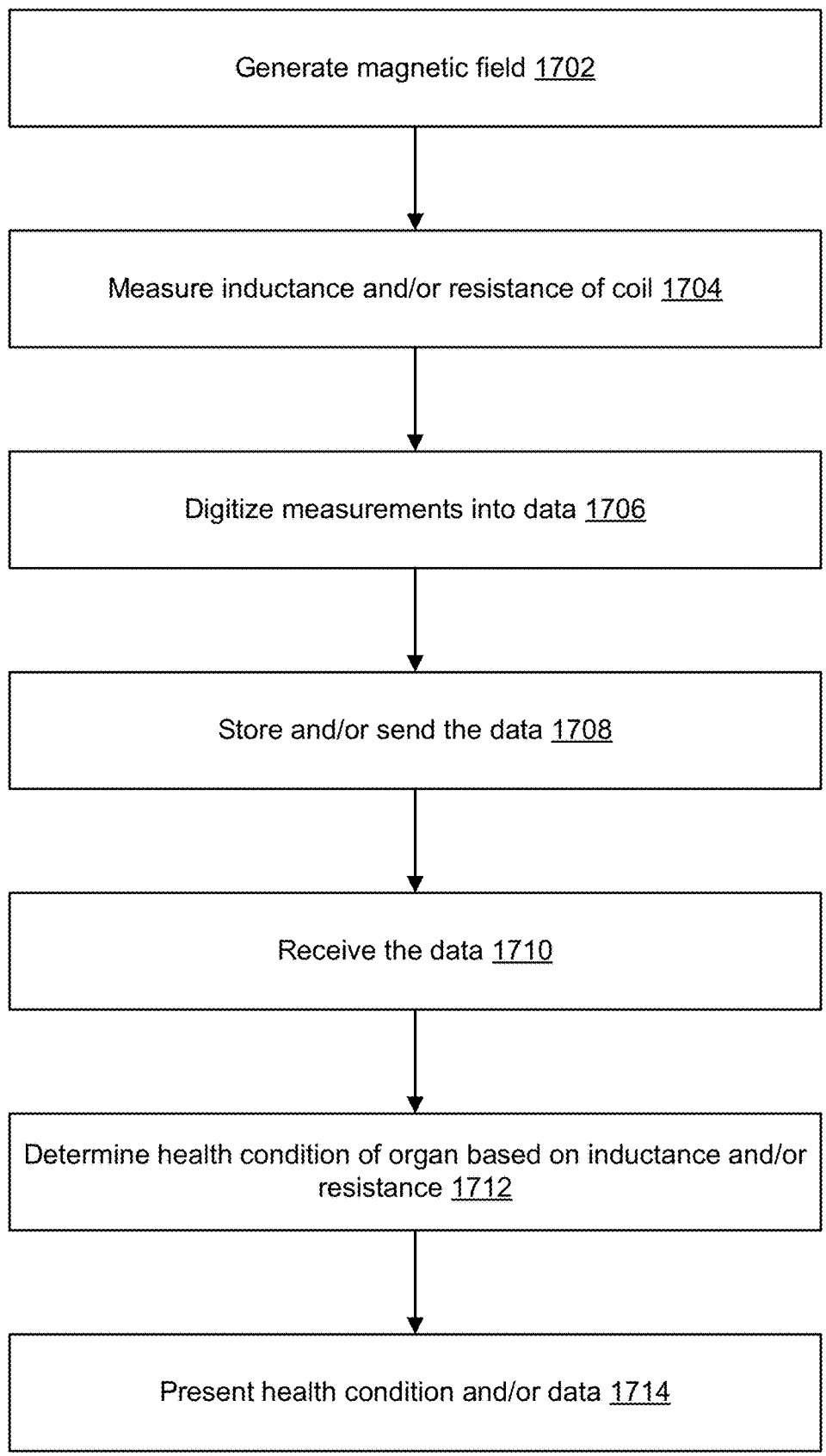
FIG. 17 illustrates an example of a flow for health diagnosis based on a sensor system in accordance with an embodiment.

FIG. 17 illustrates an example of a flow for health diagnosis based on a sensor system in accordance with an embodiment. Here also, the sensor system includes an inductive damping sensor and a computer system that may be separate from each other or integrated with each other. Although the operations of the flow of FIG. 17 are described in a particular order, the operations can be re-arranged in a different order and one or more of the operations can be skipped or omitted.

In an example, the flow of FIG. 17 starts at operation 1702, where a magnetic field is generated. For instance, the inductance sensor is worn by the subject or placed in proximity to a target organ of the subject. Upon the inductance damping sensor being powered on, a current flows through the coil, thereby generating a magnetic field. A counteracting magnetic field from the target organ changes the inductance (or equivalently the resonant frequency) and a resistance of a coil inductance damping sensor.

In an example, operation 1704 follows operation 1702. At operation 1704, at least one of the inductance (or equivalently the resonant frequency) or the resistance is measured.

For instance, a frequency counter of the inductive damping sensor measures the resonant frequency (or equivalently the inductance) and a power meter of the inductive damping sensor measures the resistance.

In an example, operation 1706 follows operation 1704. At operation 1706, the measurements are digitized into data. For instance, the frequency counter and the power meter are components of an inductance-to-digital converter that digitizes the measurements and outputs the measurement data to a microcontroller of the inductance damping sensor.

In an example, operation 1708 follows operation 1706. At operation 1708, the measurement data is stored in memory of the microcontroller and/or sent to the computer system. For instance, the measurement data can be sent in real time or near real time to the computer system or can be uploaded thereto upon demand over a wired or wireless data interface.

In an example, operation 1710 follows operation 1708. At operation 1710, the computer system receives the measurement data. For instance, the data is received from the inductive damping sensor over the data interface.

In an example, operation 1712 follows operation 1710. At operation 1712, the computer system determines a health condition of the target organ based on the at least one of the inductance (or equivalently the resonant frequency) or the resistance of the coil. For example, the computer system executes a health diagnosis application that is configured to detect the health condition given the target organ and the measurement data, as described herein above in connection with FIGS. 8-15.

In an example, operation 1714 follows operation 1712. At operation 1714, the computer system presents the health condition and/or the measurement data. For instance, the health diagnosis application presents the health condition and/or the measurement data over a user interface of the computer system.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" and "substantially" in reference to a diameter, radius, height, volume, or irradiance, wavelength, or other engineering units include measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The abstract of the disclosure is provided to allow the reader to quickly ascertain the nature of the technical disclosure. It is submitted with the understanding that it will not be used to interpret or limit the scope or meaning of the claims. In addition, in the foregoing detailed description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the detailed description, with each claim standing on its own as a separately claimed subject matter.

What is claimed is:

1. A sensor system comprising:
   an inductive damping sensor comprising:
   a coil configured to
   generate a magnetic field and
   a counteracting magnetic field in an organ located within the magnetic field; and
   an inductance-to-digital converter electrically coupled with the coil and configured to measure a least one of an inductance of the coil or a resistance of the coil based on a counteracting magnetic field from an organ located within the magnetic field; and
   a computer system communicatively coupled with the inductance-to-digital converter and comprising a processor and a memory, the memory storing computer-readable instructions that, upon execution by the processor, cause the computer system to:
   receive data from the inductance-to-digital converter; and
   determine a health condition of the organ based on the least one of inductance or resistance of the coil.

2. The sensor system of claim 1, wherein the inductance-to-digital converter is configured to measure an eddy current in the coil and output digitized data that indicates at least one of the inductance or the resistance based on the eddy current.

3. The sensor system of claim 1, wherein the coil comprises loops of a conductive wire around a cylindrical core, wherein a total number of the loops is in the range of two to fifty, and wherein a diameter of the cylindrical core is in the range of one centimeter to twenty centimeters.

4. The sensor system of claim 1, wherein the coil comprises a number of loops and has a diameter, wherein the sensor system further comprises a second inductive damping sensor, wherein the second inductive damping sensor comprises a second coil, wherein the second coil comprises a different number of loops and has a different diameter, and wherein determining the health condition comprises determining a location of the health condition within the organ based on the coil and the second coil.

5. The sensor system of claim 1, wherein determining the health condition comprises:
   determining a change in the at least one of the inductance or the resistance of the coil, wherein the change comprises at least one of a decrease of the inductance or an increase of the resistance; and
   determining a change in a conductivity of the organ based on at least one of the decrease of the inductance or the increase of the resistance.

6. The sensor system of claim 5, wherein the execution of the computer-readable instructions further configure the computer system to associate the change in the conductivity of the organ with an increase of a conductive fluid in the organ.

7. The sensor system of claim 5, wherein the execution of the computer-readable instructions further configure the computer system to associate the change in the conductivity of the organ with a volume of a conductive fluid in the organ.

8. The sensor system of claim 1, wherein determining the health condition comprises determining at least one of a location or a volume of a conductive fluid in the organ, wherein the conductive fluid causes the health condition.

9. The sensor system of claim 1, wherein determining the health condition comprises:
   determining a change in the at least one of the inductance or the resistance of the coil, wherein the change comprises at least one of an increase of the inductance or a decrease of the resistance; and
   determining a change in a conductivity of the organ based on at least one of the increase of the inductance or the decrease of the resistance.

10. The sensor system of claim 1, wherein the organ comprises a heart, and wherein the health condition comprises at least one of a blood flow of the heart, a pulse rate of the heart, or an ejection fraction of the heart.

11. The sensor system of claim 1, wherein the organ comprises a brain, and wherein the health condition comprises a hemorrhagic stroke of the brain or an ischemic stroke of the brain.

12. The sensor system of claim 1, wherein the organ comprises a brain, and wherein the health condition comprises an intracranial hemorrhage within the brain.

13. The sensor system of claim 12, wherein determining the health condition comprises:
   determining a change in the at least one of the inductance or the resistance of the coil, and
   generating a mapping of the brain based on the change in at least one of the inductance or the resistance of the coil, wherein the mapping indicates a location of the intracranial hemorrhage.

14. The sensor system of claim 1, wherein the health condition indicates skin edema based on the data indicating a decrease of the inductance or an increase of the resistance.

15. The sensor system of claim 1, wherein the health condition indicates a hemorrhage within the organ based on the data indicating a decrease of the inductance or an increase of the resistance.

16. The sensor system of claim 1, wherein the organ comprises a liver, and wherein determining the health condition comprises determining a change to a conductivity of the liver based on the data indicating a decrease of the inductance or an increase of the resistance.

17. The sensor system of claim 1, wherein the health condition indicates a respiratory rate based on the data indicating a decrease of the inductance or an increase of the resistance.

18. The sensor system of claim 1, wherein the health condition indicates location of a vein or an artery based on the data indicating a decrease of the inductance or an increase of the resistance.

19. A method of using an inductive damping sensor, the method comprising:

placing a coil connected with an inductance-to-digital converter in proximity of an organ;

generating a magnetic field through the organ using the coil;

measuring at least one of inductance or resistance of the coil based on a counteracting magnetic field from the organ located within the magnetic field; and outputting data that indicates the at least one of the inductance or the resistance; and determining a health condition of the organ based on a presentation of the data on a user interface.

20. The method of claim 19, wherein the health condition comprises at least one of: a blood flow of a heart, a pulse rate of the heart, an ejection fraction of the heart, a hemorrhagic stroke of a brain, an ischemic stroke of the brain, an intracranial hemorrhage within the brain, a skin edema, a hemorrhage, a respiratory rate, a location of a vein, or a location of an artery based on the at least one of the inductance or the resistance of the coil.

* * * * *